United States Patent
Nerurkar et al.

(10) Patent No.: US 10,726,153 B2
(45) Date of Patent: Jul. 28, 2020

(54) DIFFERENTIALLY PRIVATE MACHINE LEARNING USING A RANDOM FOREST CLASSIFIER

(71) Applicant: LeapYear Technologies, Inc., Berkeley, CA (US)

(72) Inventors: Ishaan Nerurkar, Berkeley, CA (US); Christopher Hockenbrocht, Berkeley, CA (US); Liam Damewood, Walnut Creek, CA (US); Mihai Maruseac, Berkeley, CA (US); Alexander Rozenshteyn, Berkeley, CA (US)

(73) Assignee: LeapYear Technologies, Inc., Berkeley, CA (US)

( * ) Notice: Subject to any disclaimer, the term of this patent is extended or adjusted under 35 U.S.C. 154(b) by 0 days.

(21) Appl. No.: 16/144,790

(22) Filed: Sep. 27, 2018

(65) Prior Publication Data
US 2019/0026489 A1    Jan. 24, 2019

Related U.S. Application Data

(63) Continuation-in-part of application No. 15/203,797, filed on Jul. 7, 2016, now Pat. No. 10,192,069.
(Continued)

(51) Int. Cl.
*G06F 21/62*    (2013.01)
*G06K 9/62*     (2006.01)
(Continued)

(52) U.S. Cl.
CPC ........ *G06F 21/6245* (2013.01); *G06F 16/248* (2019.01); *G06F 16/2455* (2019.01);
(Continued)

(58) Field of Classification Search
CPC ............. G06F 21/6227; G06F 21/6245; G06F 21/654; G06F 16/2455; G06F 16/248;
(Continued)

(56) References Cited

U.S. PATENT DOCUMENTS 6,546,389 B1    4/2003   Agrawal et al.
7,219,237 B1    5/2007   Trimberger
(Continued)

FOREIGN PATENT DOCUMENTS

WO   WO 2015/090445 A1   6/2015
WO   WO 2015/157020 A1   10/2015
WO   WO 2017/187207 A1   11/2017

OTHER PUBLICATIONS

Fletcher S, Islam MZ. A Differentially Private Decision Forest. In AusDM, Aug. 2015 (pp. 99-108) (Year: 2015).*
(Continued)

*Primary Examiner* — Robert B Leung
(74) *Attorney, Agent, or Firm* — Fenwick & West LLP

(57) ABSTRACT

A request from a client is received to generate a differentially private random forest classifier trained using a set of restricted data. The differentially private random forest classifier is generated in response to the request. Generating the differentially private random forest classifier includes determining a number of decision trees and generating the determined number of decision trees. Generating a decision tree includes generating a set of splits based on the restricted data, determining an information gain for each split, selecting a split from the set using an exponential mechanism, and adding the split to the decision tree. The differentially private random forest classifier is provided to the client.

17 Claims, 15 Drawing Sheets

Related U.S. Application Data

(60) Provisional application No. 62/249,938, filed on Nov. 2, 2015.

(51) Int. Cl.

| | | |
|---|---|---|
| *G16H 10/60* | (2018.01) | |
| *G06N 20/00* | (2019.01) | |
| *G06F 17/18* | (2006.01) | |
| *G06F 16/2455* | (2019.01) | |
| *G06F 16/248* | (2019.01) | |
| *G06N 20/20* | (2019.01) | |
| *G06N 5/00* | (2006.01) | |
| *G06F 17/11* | (2006.01) | |
| *G06N 20/10* | (2019.01) | |

(52) U.S. Cl.
CPC .......... *G06F 17/18* (2013.01); *G06F 21/6254* (2013.01); *G06K 9/6282* (2013.01); *G06N 5/003* (2013.01); *G06N 20/00* (2019.01); *G06N 20/20* (2019.01); *G16H 10/60* (2018.01); *G06F 17/11* (2013.01); *G06F 2221/2145* (2013.01); *G06K 9/6256* (2013.01); *G06N 20/10* (2019.01)

(58) Field of Classification Search
CPC ........ G06F 17/18; G06N 20/00; G06N 20/20; G06K 9/6282
See application file for complete search history.

(56) References Cited

U.S. PATENT DOCUMENTS

| | | |
|---|---|---|
| 7,698,250 B2 | 4/2010 | Dwork et al. |
| 10,192,069 B2 | 1/2019 | Nerurkar et al. |
| 10,229,287 B2 | 3/2019 | Nerurkar et al. |
| 2005/0278786 A1 | 12/2005 | Tippett et al. |
| 2006/0053112 A1 | 3/2006 | Chitkara et al. |
| 2006/0161527 A1 | 7/2006 | Dwork et al. |
| 2006/0200431 A1 | 9/2006 | Dwork et al. |
| 2007/0136027 A1 | 6/2007 | Dwork et al. |
| 2007/0143289 A1 | 6/2007 | Dwork et al. |
| 2007/0239982 A1 | 10/2007 | Aggarwal et al. |
| 2008/0033960 A1 | 2/2008 | Banks et al. |
| 2009/0254971 A1 | 10/2009 | Herz et al. |
| 2009/0327228 A1 | 12/2009 | Krause et al. |
| 2011/0064221 A1 | 3/2011 | McSherry et al. |
| 2011/0078143 A1 | 3/2011 | Aggarwal |
| 2011/0131222 A1 | 6/2011 | DiCrescenzo |
| 2011/0208763 A1 | 8/2011 | McSherry et al. |
| 2011/0238611 A1* | 9/2011 | McSherry ............... G06N 5/04 706/52 |
| 2011/0282865 A1 | 11/2011 | Talwar et al. |
| 2012/0143922 A1 | 6/2012 | Rane et al. |
| 2012/0197864 A1 | 8/2012 | Bourdoncle et al. |
| 2014/0088989 A1* | 3/2014 | Krishnapuram ........ G06F 19/00 705/2 |
| 2014/0214735 A1 | 7/2014 | Harik |
| 2014/0281572 A1 | 9/2014 | Wang et al. |
| 2014/0283091 A1 | 9/2014 | Zhang et al. |
| 2015/0235051 A1 | 8/2015 | Fawaz et al. |
| 2015/0286827 A1 | 10/2015 | Fawaz et al. |
| 2015/0293923 A1 | 10/2015 | Eide et al. |
| 2016/0036827 A1 | 2/2016 | Kling et al. |
| 2016/0283738 A1 | 9/2016 | Wang et al. |
| 2016/0335455 A1 | 11/2016 | Mohan et al. |
| 2017/0126694 A1 | 5/2017 | Nerurkar et al. |
| 2017/0169253 A1 | 6/2017 | Curcio et al. |
| 2017/0235974 A1 | 8/2017 | Zhang et al. |

OTHER PUBLICATIONS

Dankar, F. et al., "Practicing Differential Privacy in Health Care: A Review," Transactions on Data Privacy, 2013, vol. 5, pp. 35-67.

Extended European Search Report and Written Opinion, European Application No. 16862625.7, dated Mar. 27, 2019, 9 pages.

Frades, M.R., "Overview on Techniques in Cluster Analysis," in Bioinformatics in Clinical Research, Methods in Molecular Biology (Methods and Protocols), 2010, vol. 593, pp. 81-107.

Fraley, C. et al., "How Many Clusters? Which Clustering Method? Answers Via Model-Based Cluster Analysis," The Computer Journal, 1998, vol. 41, No. 8, pp. 578-588.

Kellaris, G. et al., "Practical differential privacy via grouping and smoothing," Proceedings of the VLDB Endowment, Mar. 1, 2013, vol. 6, No. 5, pp. 301-312.

Chaudhuri, K. et al., "Privacy-preserving logistic regression," Advances in Neural Information Processing Systems, 2009, pp. 289-296.

Zhang, J. et al., "Functional Mechanism: Regression Analysis under Differential Privacy," Proceedings of the VLDB Endowment, 2012, vol. 5, No. 11, pp. 1364-1375.

Agrawal, R. et al., "Privacy-Preserving Data Mining," ACM SIGMOD, May 2000, pp. 439-450.

Bost, R. et al. "Machine Learning Classification over Encrypted Data". NDSS '15, Feb. 8-11, 2015, pp. 1-14.

Dwork, C. et al., "Differential Privacy and Robust Statistics," Proceedings of the Forty-First Annual ACM Symposium on Theory of Computing, Nov. 14, 2008, 42 pages, [Online] [Retrieved on Sep. 15, 2016], Retrieved from the Internet<URL:http://www.stat.cmu.edu/~jingle/dprs_stoc09.pdf>.

Dwork, C. "Differential Privacy: A Survey of Results," TAMC 2008, LNCS 4978, Agrawal, M. et al. (eds.), pp. 1-19.

Dwork, C., "A Firm Foundation for Private Data Analysis," Proceedings of the ACM, Jan. 2011, 8 pages, vol. 54, Issue 1.

Dwork, C. et al., "Calibrating Noise to Sensitivity in Private Data Analysis," Proceedings of the Third Conference on Theory of Cryptography, New York, NY, Mar. 4-7, 2006, pp. 265-284.

Friedman, A. et al., "Data Mining with Differential Privacy," Proceedings of the 16th ACM SIGKDD International Conference on Knowledge Discovery and Data Mining, Dec. 2010, 11 pages, [Online] [Retrieved on Sep. 13, 2016], Retrieved from the Internet<URL:http://users.cis.flu.edu/~lzhen001/activities/KDD_USB_key_2010/docs/p493.pdf>.

Huang, Y. et al., "Telco Churn Prediction with Big Data," Proceedings of the 2015 ACM SIGMOD International Conference on Management of Data, Jun. 4, 2015, 13 pages, [Online] [Retrieved on Sep. 13, 2016], Retrieved from the Internet<URL:http://users.wpi.edu/~yli15/Includes/SIGMOD15Telco.pdf>.

Jagannathan, G. et al., "A Practical Differentially Private Random Decision Tree Classifier," International Conference on Data Mining Workshops, Proceedings of the ICDM International Workshop on the Privacy Aspects of Data Mining, 2009, pp. 114-121.

Ji, Z. et al., "Differential Privacy and Machine Learning: a Survey and Review," Cornell University Library—arXiv preprint, Dec. 24, 2014, 32 pages, [Online] [Retrieved on Sep. 14, 2016], Retrieved from the Internet<URL:http://arxiv.org/pdf/1412.7584.pdf>.

Nissim, K. et al., "Smooth Sensitivity and Sampling in Private Data Analysis," Proceedings of the Thirty-Ninth Annual ACM Symposium on Theory of Computing, Jun. 13, 2007, 11 pages, [Online] [Retrieved on Sep. 14, 2016], Retrieved from the Internet<URL:http://www.cse.psu.edu/~sxr48/pubs/smooth-sensitiviy-stoc.pdf>.

Patil, A. et al., "Differential Private Random Forest," International Conference on Advances in Computing, Communications and Informatics, Sep. 27, 2014, 10 pages, [Online] [Retrieved on Sep. 14, 2016], Retrieved from the Internet<URL:http://ieeexplore.ieee.org/stamp/stamp.jsp?tp-&arnumber=6968348&isnumber=6968191>.

PCT International Search Report and Written Opinion, PCT Application No. PCT/US16/44178, dated Oct. 18, 2016, 20 pages.

Peng, S. et al., "Query Optimization for Differentially Private Data Management Systems", ICDE Conference 2013, pp. 1093-1104.

Xiao, X. et al., "iReduct: Differential Privacy with Reduced Relative Errors", SIGMOD' 11, Jun. 12-16, 2011, pp. 229-240.

Zhang, N. et al., "Distributed Data Mining with Differential Privacy", IEEE ICC 2011 proceedings.

United States Office Action, U.S. Appl. No. 15/793,898, dated Feb. 7, 2018, 11 pages.

United States Office Action, U.S. Appl. No. 15/793,898, dated May 15, 2018, 14 pages.

(56) References Cited

OTHER PUBLICATIONS

United States Office Action, U.S. Appl. No. 15/793,907, dated Jan. 31, 2018, 11 pages.
United States Office Action, U.S. Appl. No. 15/793,907, dated May 15, 2018, 14 pages.
United States Office Action, U.S. Appl. No. 15/203,797, dated Jun. 8, 2018, 13 pages.
United States Office Action, U.S. Appl. No. 15/203,797, dated Jan. 17, 2018, 13 pages.
PCT International Search Report and Written Opinion, PCT Application No. PCT/US19/15035, dated Jun. 20, 2019, 14 pages.
Shang, S. et al., "The Application of Differential Privacy for Rank Aggregation: Privacy and Accuracy," 17th International Conference on Information Fusion, Jul. 7, 2014, pp. 1-7.
Xiao, X. et al., "Differential privacy via wavelet transforms, IEEE Transactions on Knowledge and Data Engineering," Aug. 2011, vol. 23, No. 8, pp. 1200-1214.
Xu, J. et al., "Differentially Private Histogram Publication," IEEE 28th International Conference on Data Engineering, Apr. 2012, pp. 32-43.
Amirbekyan, A. et al., "Privacy Preserving Regression Algorithms," Proceedings of the 7th WSEAS International Conference on Simulation, Modeling, and Optimization, 2007, pp. 37-45.
Cock, M.D. et al., "Fast, Privacy Preserving Linear Regression over Distributed Datasets based on Pre-Distributed Data," Proceedings of the 8th ACM Workshop on Artificial Intelligence and Security, 2015, pp. 3-14.
Du, W. et al., "Privacy-Preserving Multivariate Statistical Analysis: Linear Regression and Classification," Proceedings of the 2004 SIAM International Conference on Data Mining, 2004, pp. 222-233.
Fang, W. et al., "Privacy preserving linear regression modeling of distributed databases," Optimization Letters, 2013, vol. 7, pp. 807-818.
Han, S. et al., "Privacy-Preserving Gradient-Descent Methods," IEEE Transactions on Knowledge and Data Engineering, Jun. 2010, vol. 22, No. 6, pp. 884-899.
Sanil, A.P. et al., "Privacy Preserving Regression Modelling Via Distributed Computation," Proceedings of the Tenth ACM SIGKDD International Conference on Knowledge Discovery and Data Mining, 2004, pp. 677-682.

\* cited by examiner

| Entry # | Feature 1 (cm) | Feature 2 (residence) | | Feature 10 (age) | Feature 11 (Disease) |
|---|---|---|---|---|---|
| 1 | 163 | Italy | | 37 | 0 |
| 2 | 136 | England | | 87 | 0 |
| 3 | 180 | France | ... | 54 | 1 |
| 4 | 347 | USA | | 34 | 0 |
| 5 | 388 | China | | 18 | 0 |
| 6 | 145 | France | | 13 | 1 |
| 7 | 169 | Korea | | 65 | 1 |
| 8 | 158 | USA | | 17 | 1 |

Estimate Category

|  | | 1 | 0 |
|---|---|---|---|
| Actual Category | 1 | True Positive | False Negative |
|  | 0 | False Positive | True Negative |

700

DIFFERENTIALLY PRIVATE MACHINE LEARNING USING A RANDOM FOREST CLASSIFIER

CROSS-REFERENCE TO RELATED APPLICATIONS

This application is a continuation-in-part of application Ser. No. 15/203,797, filed Jul. 7, 2016, which claims the benefit of Provisional Application No. 62/249,938, filed Nov. 2, 2015, both of which are incorporated by reference herein.

BACKGROUND

Field of Disclosure

The present invention generally relates to building classifiers used in computerized machine learning, and more specifically to preserving privacy of training data used to build a machine-learned classifier.

Description of the Related Art

Data about people, such as health data, financial records, location information, web browsing, and viewing habits, is valuable for analysis and collaboration. There are many technologies in which statistical or predictive analysis of personal data is beneficial. For example, medical research institutions use medical information about populations of individuals to support epidemiologic studies. Map providers use location information gathered from mobile devices carried by people to determine traffic information and provide routing guidance. Technology companies collect information describing behaviors of Internet users to improve their offerings, such as by redesigning user interfaces to improve human-computer interactions, making improved recommendations, and offering sponsored messages.

However, the personal nature of this data limits its usefulness. Government regulations provide strict rules about how personal data can be collected, used, and shared. Individuals also have expectations about how their personal data will be used, and may react negatively if it is publicly disclosed. As a result, companies that collect and maintain personal data seek ways to extract value from it without running afoul of such rules and expectations.

One set of techniques for using personal data involves limiting access to the raw data. Access controls may be used to restrict access to only individuals having appropriate credentials. Another set of techniques involves removing personally-identifiable information from the data through masking, hashing, anonymization, aggregation, and tokenization. These techniques tend to be resource intensive and may compromise analytical utility. For example, data masking may remove or distort data, compromising the statistical properties of the data.

An additional technique makes use of differential privacy. Differential privacy is technology that injects noise into results provided by statistical databases in order to protect private information. Within this technological space, issues arise over how to add noise in view of different use cases, and how much noise to add. The answers to these questions can be complex due to the potential resources available to determined adversaries (e.g., the computing power available to a potential attacker trying to gain access to the private data), the resources (e.g., computing power) available to the database, and the types of queries supported by the database.

One particular use case in which these issues arise is machine learned classification. Here, known properties from training data are used to build statistical models, called "classifiers," that can map new data into one or more output classifications. Often, the training data contains private information. For example, the training data may describe medical histories of a patient population and be used to generate a classifier for detecting a particular medical condition. Absent a privacy-protection mechanism such as differential privacy, a determined adversary may be able to derive at least some of the private information within the training data through examination of a machine-learned classifier.

SUMMARY

A differentially private security system is communicatively coupled to a database including restricted data. The differentially private security system receives a request from a client to generate a differentially private random forest classifier based on the restricted data and identifies a level of differential privacy corresponding to the request. The identified level of differential privacy includes a privacy parameter c indicating the degree of information released about the database by performance of the query.

The differentially private security system generates the differentially private random forest classifier in response to the request. Generating the differentially private random forest classifier includes determining a number of decision trees and generating the determined number of decision trees. Generating a decision tree includes generating a set of splits based on the restricted data, determining an information gain for each split, selecting a split from the set using an exponential mechanism, and adding the split to the decision tree. The differentially private random forest classifier is provided to the client.

BRIEF DESCRIPTION OF DRAWINGS

FIG. 2 illustrates an example database structure, according to one embodiment.

The figures depict embodiments of the invention for purposes of illustration only. One skilled in the art will readily recognize from the following description that alternative embodiments of the structures and methods illustrated herein may be employed without departing from the principles of the invention described herein.

DETAILED DESCRIPTION

Reference will now be made in detail to several embodiments, examples of which are illustrated in the accompanying figures. It is noted that wherever practicable similar or like reference numbers may be used in the figures and may indicate similar or like functionality.

System Overview

Figure 1:
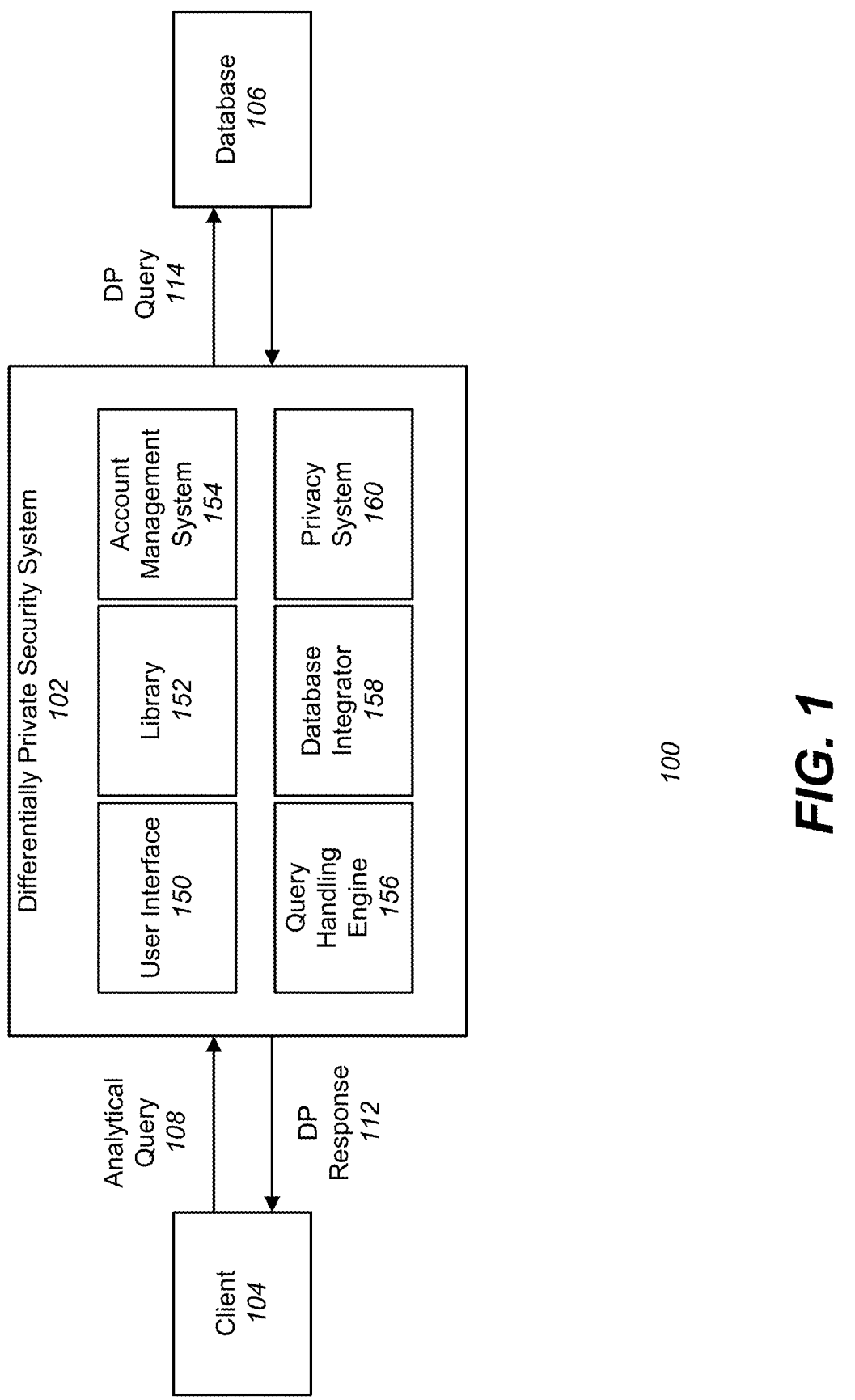
FIG. 1 illustrates a system for receiving a query for a private database, and for responding to the query by executing a differentially private version of the query on the private database.

FIG. 1 is a system 100 for receiving a query 108 for a database 106, and responding to the query 108 by executing the query in a differentially private (DP) manner. The system 100 includes a differentially private security system 102 that receives the analytical query 108 from a client 104 and applies a DP version of the query 114 on the database 106. Subsequently, the differentially private security system 102 returns the response of the DP query 114 to the client 104 as the DP response 112.

The database 106 is one or more databases managed by one or more entities. The database 106 may be managed by the same entity that manages the differentially private security system 102 or by a different entity. The database 106 stores at least some restricted data. The restricted data may be represented as rows of records, with each record having a set of columns holding values pertaining to the record.

Restricted data is data to which access and/or usage is limited due to legal, contractual, and/or societal concerns. Examples of restricted data include health data of patients and financial records of people, businesses or other entities. Similarly, restricted data may include census data or other forms of demographic data describing people, businesses, or other entities within geographic areas. Restricted data also includes usage data describing how people interact with electronic devices and/or network-based services. For example, restricted data may include location data describing geographic movements of mobile devices, consumption history data describing how and when people consume network-based content, and the particular content consumed (e.g., music and/or video content), and messaging data describing when and to whom users send messages via mobile or other electronic devices.

A client 104 is used to access the restricted data in the database 106. A client 104 is an electronic device such as a desktop, laptop, or tablet computer or a smartphone used by a human user to access the database 106. The client 104 and user may be, but are not necessarily, associated with the entities that manage the database 106 and/or differentially private security system 102. Users of the client 104 include administrators and analysts. Administrators use the clients 104 to access the differentially private security system 102 and/or database 106 to perform administrative functions such as provisioning other users and/or clients 104, and configuring, maintaining, and auditing usage of the system and/or database. The administrators may access the differentially private security system 102 and database 106 directly via administrative interfaces that allow users with appropriate credentials and access rights to perform the administrative functions.

Analysts use the clients 104 to apply analytical queries 108 to the restricted data in the database 106. The clients 104 used by the analysts access the database 106 only through the differentially private security system 102. Depending upon the embodiment, the analyst and/or client 104 may have an account provisioned by an administrator which grants the analyst or client certain rights to access the restricted data in the database 106.

The rights to the restricted data may be specified in terms of a privacy budget. The privacy budget describes limits on how much of the restricted data can be released. In one embodiment, the privacy budget is a numerical value representative of a number and/or type of remaining queries 108 available. The privacy budget may be specified in terms of a query, analyst, client 104, entity, globally, and/or time period. For example, the privacy budget may specify limits for an individual query, with each query having a separate budget. The privacy budget may also specify limits for an analyst or client, in which case the budget is calculated cumulatively across multiple queries from a client or analyst. For a privacy budget specified for an entity, such as an organization having multiple clients 104 and users, the privacy budget is calculated cumulatively across the multiple queries from clients and users associated with the entity. A global privacy budget, in turn, is calculated across all queries to the database, regardless of the source of the query. The privacy budget may also specify an applicable time period. For example, the privacy budget may specify that queries from particular sources (e.g., analysts, entities) may not exceed a specified budget within a given time period, and the budget may reset upon expiration of the time period.

As discussed above, a client 104 sends an analytical query 108 to the differentially private security system 102 and also receives a differentially private response 112 to the query from the system. The queries 108 submitted by the client 104 may be simple queries, such as count queries that request the number of entries in the databases 106 that satisfy a condition specified by the client 104, or complicated queries, such as predictive analytics queries that request a data analytics model trained on the databases 106. Specific types of queries are discussed in more detail below.

Each query has an associated set of privacy parameters. The privacy parameters indicate the amount of restricted data to release from the database 106 to the client 104 in response to the query 108. The privacy parameters likewise indicate the amount of decrease in the relevant privacy budget (e.g., the budget for the client 104 or entity with which the client is associated) in response to the query 108. In one embodiment, the client 104 specifies a set of associated privacy parameters with each submitted query 108. In other embodiments, the privacy parameters are specified in other ways. The differentially private security system 102 may associate privacy parameters with received queries (rather than obtaining the parameters directly from the query). For example, the differentially private security system 102 may apply a default set of privacy parameters to queries that do not specify the parameters. The values of the default privacy parameters may be determined based on the client 104, analyst, query type, and/or other factors.

The differentially private security system 102 receives an analytical query 108 from the client 104 and returns a differentially private response 112 to the client. In one embodiment, the differentially private security system 102 determines the privacy parameters associated with the query, and evaluates the parameters against the applicable privacy budget. If the analytical query 108 and associated privacy parameters exceeds the privacy budget, the differentially private security system 102 may deny (i.e., not execute) the query. Alternatively, the differentially private security system 102 may adjust the privacy parameters to fall within the privacy budget, and execute the query using the adjusted privacy parameters. If the privacy parameters do not exceed the privacy budget, the differentially private security system 102 executes a DP version of the query 114 on the database 106, such that it releases a degree of restricted data from the database 106 indicated by the privacy parameters specified by the client 104, and also protects a degree of privacy of the restricted data specified by the privacy budget. For example, an administrator of the database 106 may set a privacy budget specifying a maximum threshold on the amount of restricted data released by given query 108 that the client 104 may not exceed. Thus, the differentially private security system 102 balances privacy protection of the restricted data in the database 106 while releasing useful information on the database 106 to the client 104.

The DP query 114 applied to the database 106 by the differentially private security system 102 is a differentially private version of the query 108 that satisfies a definition of differential privacy described in more detail with reference to the privacy system 160 in FIG. 3. The differentially private security system 102 may apply the DP query 114 to the database 106 by transforming the analytical query 108 into one or more queries derived from the analytical query that cause the database 106 to release differentially private results. The differentially private security system 102 may then return these differentially private results to the client as the DP response 112. The differentially private security system 102 may also, or instead, apply the DP query 114 to the database 106 by transforming the analytical query into one or more derived queries that cause the database to release results that are not necessarily differentially private. The differentially private security system 102 may then transform the released results in a way that enforces differential privacy to produce the DP response 112 returned to the client 104. These transformations may involve perturbing the process by which the DP query 114 is produced from the analytical query 108 and/or the perturbing the results released by the database 106 with noise that provides the differential privacy specified by the privacy parameters while enforcing the privacy budget.

The differentially private security system 102 allows an analyst to perform database queries on restricted data, and thereby perform analyses using the DP responses 112 returned by the queries, while maintaining adherence with privacy parameters and a privacy budget. In addition, the techniques used by the differentially private security system 102 allow database queries to access restricted data in ways that do not compromise the analytical utility of the data. The differentially private security system 102 supports a wide variety of analytical and database access techniques, described in more detail below, and provides fine-grained control of the privacy parameters and privacy budget when using such techniques. The differentially private security system 102 thus provides an improved database system having expanded and enhanced access to restricted data relative to other database systems.

An analyst can use the differentially private security system 102 for a variety of different purposes. In one embodiment, the restricted data in the database 106 includes training data describing features of entities relevant to a particular condition. The analyst uses the differentially private security system 102 to build one or more differentially private machine-learned models, such as classifiers, from the training data. The analyst can apply data describing a new entity to the machine-learned models, and use the outputs of the models to classify the new entity as having, or not having the condition. However, an adversary cannot use the information in the machined-learned models to ascertain whether individual entities described by the training set have the condition due to the differentially private nature of the models.

Such models may be retained and executed within the differentially private security system 102. For example, an analyst can issue an analytical query 108 that causes the differentially private security system 102 to interact with the restricted data in the database 106 to build the machine-learned models. The differentially private security system 102 can then store the models within the system or an associated system. The analyst can use a new analytical query 108 or another interface to the system 102 to apply the data describing the new entity to the models. The differentially private security system 102 can execute the new data on the stored models and output the classification of the entity as a DP response 112. Alternatively or in addition, the differentially private security system 102 can output the trained models as a DP response 112, and an analyst can store and apply data to the models using different systems in order to classify the entity.

Examples of the types of classifications that may be performed using such models include determining whether a person (the entity) has a medical condition. In this example, the restricted training data include health data describing patients that are labeled as having or not having a given medical condition. The analyst applies health data for a new patient to the one or more differentially private machine-learned models generated from the restricted training data in order to diagnose whether the new patient has the medical condition.

Another example classification that may be performed using such models involves identifying fraudulent or otherwise exceptional financial transactions. In this example, the restricted training data includes financial transaction data associated with one or more people or institutions, where the transactions are labeled as being exceptional or not exceptional. The analyst applies financial transaction data for a new transaction to the one or more differentially private machine-learned models generated from the restricted training data in order to determine whether the new transaction is exceptional. The analyst can block, flag, or otherwise report an exceptional transaction.

Returning to the discussion of FIG. 1, the differentially private security system 102 includes a user interface 150, a library 152, an account management system 154, a query handling engine 156, a data integration module 158, and a privacy system 160. Some embodiments of the differentially private security system 102 have different or additional modules than the ones described here. Similarly, the functions can be distributed among the modules in a different manner than is described here. Certain modules and functions can be incorporated into other modules of the differentially private security system 102.

The user interface 150 generates a graphical user interface on a dedicated hardware device of the differentially private security system 102 or the client 104 in which the client 104 can submit an analytical query 108 and the desired privacy parameters, view the DP response 112 in the form of numerical values or images, and/or perform other interactions with the system. The client 104 may also use the graphical user interface to inspect the database 106 schemata, view an associated privacy budget, cache the DP response 112 to view the response later, and/or perform administrative functions. The user interface 150 submits properly formatted query commands to other modules of the differentially private security system 102.

The library 152 contains software components that can be included in external programs that allow the client 104 to submit the analytical query 108, receive the DP response 112, and other functions within a script or program. For example, the client 104 may use the software components of the library 152 to construct custom data analytic programs. Each of the software components in the library 152 submits properly formatted query commands to other modules of the differentially private security system 102.

The account management system 154 receives properly formatted query commands (herein "query commands" or "QC"), parses the received query commands, and updates the account of the client 104 according to the received query command. For example, the account management system 154 may check the query commands for syntactic correctness, and/or check whether a client 104 has access to a requested resource. As another example, the account management system 154 may check whether the privacy parameters specified by the client 104 for a given analytical query 108 can be accommodated, and if so, decrement the privacy budget of the client 104 by the amount specified in the query 108. Query commands verified by the account management system 154 are provided to the query handling engine 156. Examples of query commands accommodated by the differentially private security system 102 are listed below.

QC1. Count
'SELECT COUNT (<column>) FROM<database.table> WHERE<where_clause> BUDGET <eps> <delta>.

QC2. Median
'SELECT MEDIAN (<column>) FROM<database.table> WHERE<where_clause> BUDGET <eps> <delta>.

QC3. Mean
'SELECT MEAN (<column>) FROM <database.table> WHERE <where_clause> BUDGET <eps> <delta>.

QC4. Variance
'SELECT VARIANCE (<column>) FROM <database.table> WHERE <where_clause> BUDGET <eps> <delta>.

QC5. Inter-Quartile Range
'SELECT IQR (<column>) FROM <database.table> WHERE <where_clause> BUDGET <eps> <delta>.

QC6. Batch Gradient Descent
'SELECT <GLM> (<columns_x>,<column_y>,<params>) FROM <database.table> WHERE <where_clause> BUDGET <eps> <delta>.

QC7. Stochastic Gradient Descent
'SELECT SGD <GLM>(<column>) FROM <database.table> WHERE <where_clause> BUDGET <eps> <delta>.

QC8. Random Forest
'SELECT RANDOMFOREST (<columns_x>,<columns_y>) FROM <database.table> WHERE <where_clause> BUDGET <eps> <delta>.

QC9. Histogram
'SELECT HISTOGRAM (<column>) FROM <database.table> WHERE <where_clause_i> BUDGET <eps> <delta>.

The query handling engine 156 transforms the received query commands into appropriate function calls and database access commands by parsing the query command string. The function calls are specific to the query 108 requested by the client 104, and the access commands allow access to the required database 106. Different databases 106 require different access commands. The access commands are provided to the database integrator 158.

The database integrator 158 receives the access commands to one or more databases 106, collects the required databases, and merges them into a single data object. The data object has a structure similar to that of a database structure described in reference to FIG. 2. The data object is provided to the privacy system 160.

The privacy system 160 receives the data object from the database integrator 158, appropriate function calls from the query handling engine 156 indicating the type of query 108 submitted by the client 104, and privacy parameters specified for the query 108. The privacy system 160 evaluates the privacy parameters against the applicable privacy budget and either blocks or allows the query. If the query is blocked, the privacy system 160 may return a response to the client 104 indicating that the query did not execute. If the query is allowed, the privacy system 160 produces a DP response 112 to a differentially private version of the query 108 with respect to the databases 106. The privacy system 160 will be described in further detail in reference to FIG. 3 below.

FIG. 2 illustrates an example database structure, according to one embodiment. For the remainder of the application, a database, including one or more of the databases 106, may be referred to as a matrix with a number of rows and columns. Each row is an entry of the database and each column is a feature of the database. Thus, each row contains a data entry characterized by a series of feature values for the data entry. For example, as shown in FIG. 2, the example database 200 contains 8 entries and 11 features, and illustrates a list of patient profiles. Each patient is characterized by a series of feature values that contain information on the patient's height (Feature 1), country of residence (Feature 2), age (Feature 10), and whether the patient has contracted a disease (Feature 11). A row is also referred to as a "record" in the database 106.

The feature values may be numerical in nature, e.g., Features 1 and 10, or categorical in nature, e.g., Features 2 and 11. In the case of categorical feature values, each category may be denoted as an integer. For example, in Feature 11 of FIG. 2, "0" indicates that the patient has not contracted a disease, and "1" indicates that the patient has contracted a disease.

Privacy System

Figure 3:
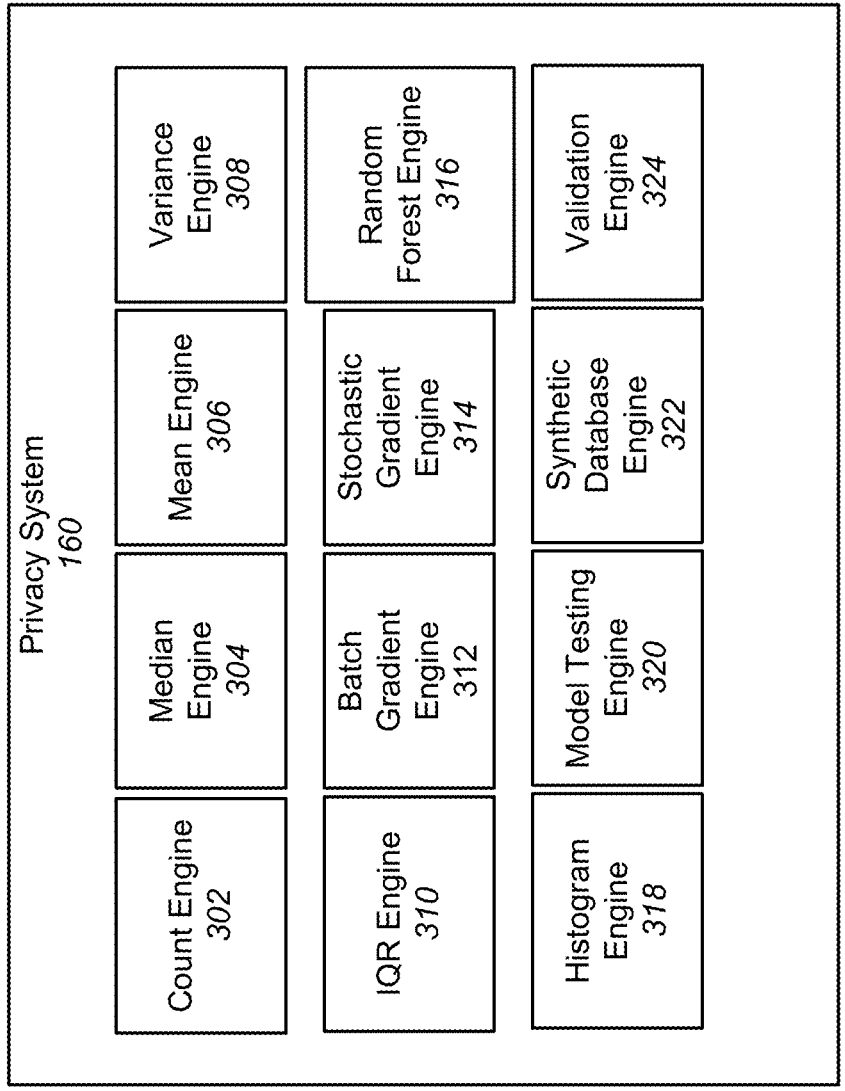
FIG. 3 is a block diagram illustrating the privacy system of the system in FIG. 1, according to one embodiment.

FIG. 3 is a block diagram illustrating the privacy system 160 of the system 100 shown in FIG. 1, according to one embodiment. The privacy system 160 includes a count engine 302, a mean engine 304, a median engine 306, a variance engine 308, an IQR engine 310, a batch gradient engine 312, a stochastic gradient engine 314, a random forest engine 316, a histogram engine 318, a model testing engine 320, a synthetic database engine 322, and a validation engine 324. Some embodiments of the privacy system 160 have different or additional modules than the ones described here. Similarly, the functions can be distributed among the modules in a different manner than is described here. Certain modules and functions can be incorporated into other modules of the privacy system 160.

Definition of Differential Privacy

For a given query 108, the privacy system 160 receives a data object X, function calls indicating the type of query 108, privacy parameters specified by the client 104, and outputs a DP response 112 to a differentially private version of the query 108 with respect to X. Each data object X is a collection of row vectors $x_{i=1, 2, \ldots, n}$, in which each row vector $x_i$ has a series of p elements $x_i^{i=1, 2, \ldots p}$.

A query M satisfies the definition of ε-differential privacy if for all:

$$\forall X, X' \in \mathbb{D}, \forall S \subseteq \text{Range}(M): \frac{Pr[M(X) \in S]}{Pr[M(X') \in S]} \leq e^\varepsilon$$

where $\mathbb{D}$ is the space of all possible data objects, X, X' neighboring data objects, S is an output space of query M, and neighboring databases are defined as two data objects X, X' that have at most one different entry from one another. That is, given two neighboring data objects X, X' in which one has an individual's data entry, and the other does not, there is no output of query M that an adversary can use to distinguish between X, X'. That is, an output of such a query M that is differentially private reveals no information about the data object X. The privacy parameter E controls the amount of information that the query M reveals about any individual data entry in X, and represents the degree of information released about the entries in X. For example, in the definition given above, a small value of E indicates that the probability an output of query M will disclose information on a specific data entry is small, while a large value of ε indicates the opposite.

As another definition of differential privacy, a query M is (ε,δ)-differentially private if for neighboring data objects X, X':

$$\forall X, X' \in \mathbb{D}, \forall S \subseteq \text{Range}(M): \frac{Pr[M(X) \in S]}{Pr[M(X') \in S]} \leq e^\varepsilon + \delta.$$

The privacy parameter δ measures the improbability of the output of query M satisfying ε-differential privacy. As discussed in reference to FIG. 1, the client 104 may specify the desired values for the privacy parameters (ε,δ) for a query 108.

There are three important definitions for discussing the privacy system 160: global sensitivity, local sensitivity, and smooth sensitivity. Global sensitivity of a query M is defined as $$GS_M(X) = \max_{X, X': d(X, X')=1} \|M(X) - M(X')\|$$

where X, X' are any neighboring data objects, such that d(X, X')=1. This states that the global sensitivity is the most the output of query M could change by computing M on X and X'.

The local sensitivity of a query M on the data object X is given by:

$$LS_M(X) = \max_{X': d(X, X')=1} \|M(X) - M(X')\|$$

where the set {X': d(X, X')=1} denotes all data objects that have at most one entry that is different from X. That is, the local sensitivity $LS_M(X)$ is the sensitivity of the output of the query M on data objects X' that have at most one different entry from X, measured by a norm function.

Related to the local sensitivity $LS_M(X)$, the smooth sensitivity given a parameter β is given by:

$$S_M(X; \beta) = \max_{X' \in \mathbb{D}} \|LS_M(X) \cdot e^{-\beta \cdot d(X, X')}\|$$

where d(X, X') denotes the number of entries that differ between X and X'.

Notation for Random Variables

The notation in this section is used for the remainder of the application to denote the following random variables.

1) $G(\sigma^2)$, denotes a zero-centered Gaussian random variable with the probability density function $$f(x | \sigma^2) = \frac{1}{\sigma\sqrt{2\pi}} e^{-\frac{x^2}{2\sigma^2}}.$$

2) L(b) denotes a zero-centered Laplacian random variable with the probability density function $$f(x | b) = \frac{1}{2b} e^{-\frac{|x|}{b}}.$$

3) C(γ) denotes a zero-centered Cauchy random variable with the probability density function $$f(x | y) = \frac{1}{\pi\gamma\left(1 + \left(\frac{x}{\gamma}\right)^2\right)}.$$

Further, a vector populated with random variables R as its elements is denoted by v(R). A matrix populated with random variables R as its elements is denoted by M(R).

Count Engine 302

The count engine 302 produces a DP response 112 responsive to the differentially private security system 102 receiving a query 108 for counting the number of entries in a column of the data object X that satisfy a condition specified by the client 104, given privacy parameters (ε,δ). An example query command for accessing the count engine 302 is given in QC1 above. For the example data object X shown in FIG. 2, the client 104 may submit a query 108 to return a DP response 112 for the number of patients that are above the age of 30.

The count engine 302 retrieves the count q from X. If privacy parameter δ is equal to zero, the count engine 302 returns $$y \approx q + L\left(c_1 \cdot \frac{1}{\epsilon}\right),$$

as the DP response 112 for display on the user interface 150, where $c_i$ is a constant. An example value for $c_i$ may be 1. If the privacy parameter $\delta$ is non-zero, the count engine 302 returns $$y \approx q + G\left(c_1 \cdot 2 \cdot \log\frac{2}{\delta} \cdot \frac{1}{\epsilon^2}\right),$$

as the DP response 112 for display on the user interface 150, where $c_i$ is a constant. An example value for $c_i$ may be 1.

Figure 4:
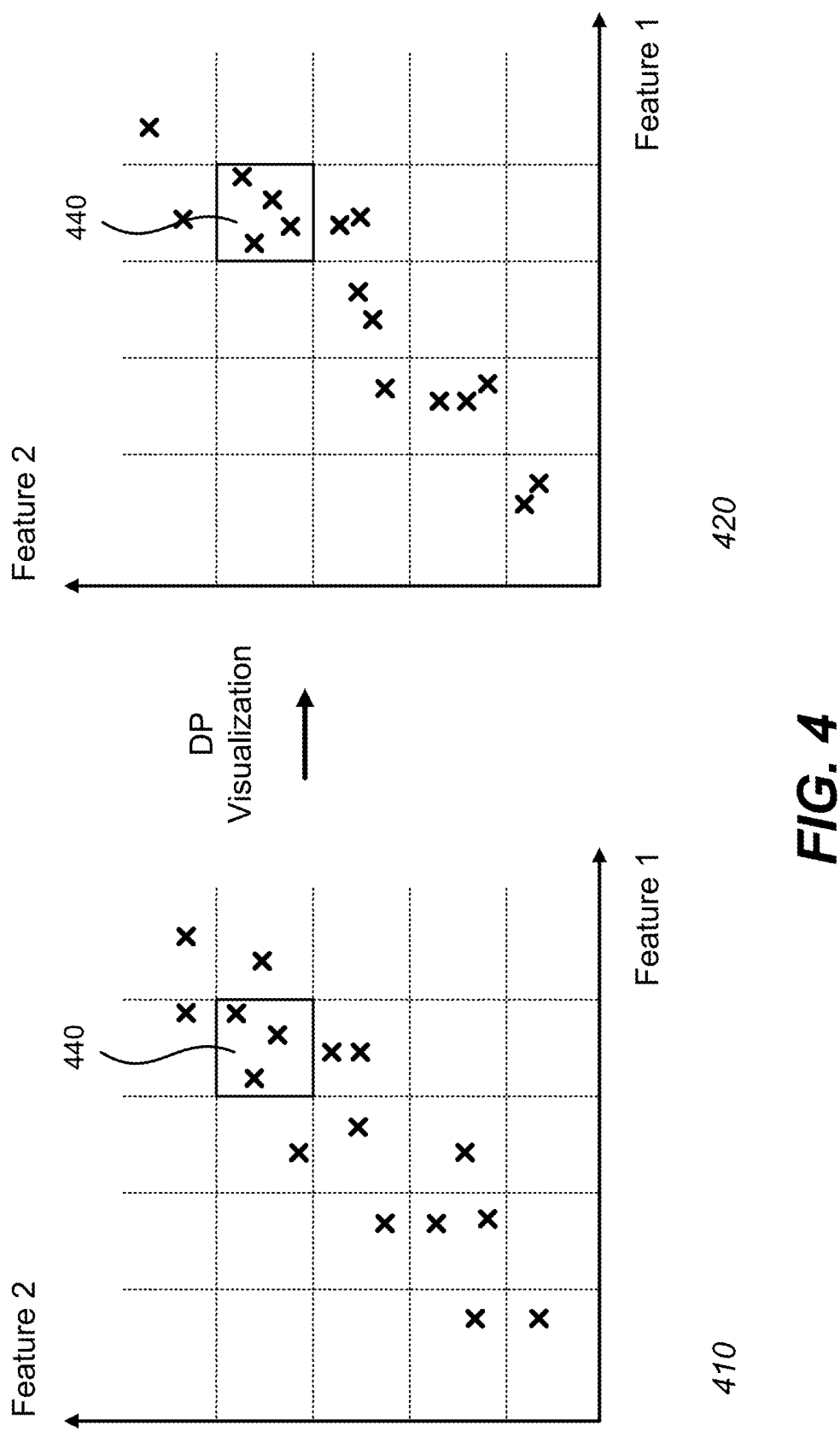
FIG. 4 illustrates displaying results of a differentially private count query, according to one embodiment.

The client 104 may request visualization of entries in the data object X for analysis of trends or patterns that depend on the features of the entries. In one embodiment, the privacy system 160 generates a differentially private visualization of the requested data entries from X. FIG. 4 illustrates displaying results of a differentially private count query to the user interface of the client, according to one embodiment.

The privacy system 160 first maps the requested entries from X for the selected features specified by the client 104. For example, as shown in the visualization 410 of FIG. 4, a series of requested entries are plotted depending on their values for Feature 1 and Feature 2. The privacy system 160 then generates disjoint regions on the plot and retrieves the counts of entries in each of the disjoint regions. In visualization 410, the privacy system 160 divides the plot into disjoint squares and retrieves the count of entries in each square.

For each disjoint region, the privacy system 160 submits a differentially private count query to the count engine 302, and randomly plots a number of entries determined by the DP response 112 of the count engine 302 for that region. The resulting DP visualization plot is returned to the client 104 for display to a user by the user interface 150. For example, square 440 in visualization 410 contains 3 entries, while the same square in DP visualization 420 contains 4 randomly plotted entries determined by the DP response 112 of the count engine 302.

Median Engine 304

The median engine 304 produces a DP response 112 responsive to the differentially private security system 102 receiving a query 108 for generating the median of entries in a column of the data object X that satisfy a condition specified by the client 104, given privacy parameters $(\epsilon,\delta)$. An example query command for accessing the median engine 304 is given in QC2 above. For the example data object X shown in FIG. 2, the client 104 may submit a query 108 to return a DP response 112 for the median age of all patients in X.

The median engine 304 aggregates the values of entries satisfying the condition specified by the client 104 into a list U, and retrieves the median q from U. If privacy parameter $\delta$ is equal to zero, the median engine 304 returns $$y \approx q + c_1 \cdot S_M(U; c_2 \cdot \epsilon) \cdot \frac{C(1)}{\epsilon}$$

as the DP response 112 for display on the user interface 150, in which $c_1, c_2$ are constant factors. Example values for $c_1, c_2$ may be 6 and 1/6, respectively. If $\delta$ is non-zero, the median engine 304 returns $$y \approx q + c_1 \cdot S_M\left(U; c_2 \cdot \frac{\epsilon}{2 \cdot \log\frac{1}{\delta}}\right) \cdot \frac{L(1)}{\epsilon}$$

as the DP response 112 for display on the user interface 150. Example values for $c_1, c_2$ may be 2 and 1, respectively.

Mean Engine 306

The mean engine 306 produces a DP response 112 responsive the differentially private security system 102 receiving a query 108 for generating the mean of entries in a column of the data object X that satisfy a condition specified by the client 104, given privacy parameters $(\epsilon,\delta)$. An example query command for accessing the mean engine 306 is given in QC3 above. For the example data object X shown in FIG. 2, the client 104 may submit a query 108 to return a DP response 112 for generating the mean age of patients that are above the age of 30.

The mean engine 306 aggregates the values of entries satisfying the condition specified by the client 104 into a list U. Assuming there are n values in U, the mean engine 306 further divides U into m sub-lists $V_{j=1, 2, \ldots, m}$ each with n/m values. The mean engine 306 aggregates each mean $r_j$ of sub-list $V_j$ into a list R. The mean engine 306 requests a differentially private median query of the values in R to the median engine 304. The resulting output from the median engine 304 is returned as the DP response 112 for display on the user interface 150.

Variance Engine 308

The variance engine 308 produces a DP response 112 responsive to the differentially private security system 102 receiving a query 108 for generating the variance of entries in a column of the data object X that satisfy a condition specified by the client 104, given privacy parameters $(\epsilon,\delta)$. An example query command for accessing the variance engine 308 is given in QC4 above. For the example data object X shown in FIG. 2, the client 104 may submit a query 108 to return a DP response 112 for generating the variance of the age of all patients in X.

The variance engine 308 aggregates the values of entries satisfying the condition specified by the client 104 into a list U. Assuming there are n values in U, the variance engine 308 further divides U into m sub-lists $V_{j=1, 2, \ldots, m}$ each with n/m values. The variance engine 308 aggregates each variance $r_j$ of sub-list $V_j$ into a list R. The variance engine 308 requests a differentially private median query of the values in R to the median engine 304. The resulting output from the median engine 304 is returned as the DP response 112 for display on the user interface 150.

IQR Engine 310

The IQR engine 310 produces a DP response 112 responsive to the differentially private security system 102 receiving a query 108 for generating the interquartile range (IQR) of entries in a column of the data object X that satisfy a condition specified by the client 104, given privacy parameters $(\epsilon,\delta)$. An example query command for accessing the IQR engine 310 is given in QC5 above. For the example data object X shown in FIG. 2, the client 104 may submit a query 108 to return a DP response 112 for generating the IQR of the age of all patients in X.

In one embodiment, the IQR engine 310 aggregates the values of entries satisfying the condition specified by the client 104 into a list U. Assuming there are n values in U, the sample IQR of U is denoted as IQR(U), and a log transform of IQR(U) is denoted as:

$$H_n(U) = \log_{1+\frac{1}{\log n}} IQR(U).$$

The IQR engine 310 further maps the quantity $H_n(U)$ to an integer $k_0$ such that $H_n(U) \in [k_0, k_0+1)$. The IQR engine 310 extracts a value $A_0(U)$ indicating the number of entries in U required to change in order for the new list $\tilde{U}$ to satisfy $H_n(\tilde{U}) \notin [k_0, k_0+1)$.

The IQR engine 310 then generates a value $R_0(U)$ given by:

$$R_0(U) \approx A_0(U) + L\left(\frac{c_1}{\epsilon}\right)$$

in which $c_1$ is a constant factor. If $R_0(U)$ is greater than a predetermined threshold, the IQR engine 310 returns $$y = IQR(U) \cdot \left(\frac{1}{1+\log n}\right)^{L\left(\frac{c_1}{\epsilon}\right)},$$

as the DP response 112 for display on the user interface 150. If $R_0(U)$ is equal to or less than the predetermined threshold, the IQR engine 310 returns "No Answer" as the DP response 112 for display on the user interface 150.

In another embodiment, the IQR engine 310 aggregates the values of entries satisfying the condition specified by the client 104 into an ordered list $\underline{U}$. The IQR engine 310 retrieves the first quartile and the third quartile from U, given by q and q', respectively. If δ is zero, the IQR engine 310 returns:

$$y \approx \left(q + c_1 \cdot S_M(U; c_2 \cdot \epsilon) \cdot \frac{C(1)}{\frac{\epsilon}{2}}\right) - \left(q' + c_1 \cdot S_M(U; c_2 \cdot \epsilon) \cdot \frac{C(1)}{\epsilon/2}\right)$$

as the DP response 112 for display on the user interface 150, in which $c_1$, $c_2$ are constant factors.

If δ is non-zero, the IQR engine 310 returns:

$$y \approx \left(q + c_1 \cdot S_M\left(U; c_2 \cdot \frac{\epsilon}{2 \cdot \log\frac{1}{\delta}}\right) \cdot \frac{L(1)}{\epsilon/2}\right) - \left(q' + c_1 \cdot S_M\left(U; c_2 \cdot \frac{\epsilon}{2 \cdot \log\frac{1}{\delta}}\right) \cdot \frac{L(1)}{\epsilon/2}\right)$$

as the DP response 112 for display on the user interface 150, in which $c_1$, $c_2$ are constant factors.

Batch Gradient Engine 312

The batch gradient engine 312 produces a DP response 112 responsive to the differentially private security system 102 receiving a valid query 108 for generating a set of parameters θ for a general linear model that captures the correlation between a series of observable features and a dependent feature, given privacy parameters (ε,δ). The general linear model is trained on the selected columns of X. An example query command for accessing the match gradient engine 312 is given in QC6 above.

Given a row vector x that contains a series of observable features and a label feature y, the correlation between the observable features and the label feature in a general linear model may be given as:

$$y = x\theta^T,$$

where θ is a row vector containing parameters of the model. That is, the label feature is modeled as a weighted sum of the observable features, where each value in θ is the weight given to a corresponding observable feature.

For the example data object X shown in FIG. 2, the client 104 may submit a query 108 to return a DP response 112 for generating a set of parameters θ for a general linear model that captures the correlation between the height of the patients (observable feature) and the age of the patients (label feature). As another example, the features may be categorical in nature, and the requested parameters θ may be for a general linear model that captures the correlation between the height, age, residence of the patients (observable features) and whether the patient will or has contracted a disease (label feature).

Examples of general linear models supported by the batch gradient engine 312 are, but not limited to, linear regression, logistic regression, and support vector machine (SVM) classifiers.

The optimal values for the set of parameters θ is found by training the general linear model on training data (Xtrain, ytrain) consisting of selected columns of data object X. Specifically, $X_{train}$ is a matrix database in which each column corresponds to a selected observable feature, and y is a column vector of the selected label feature values. Each entry in $X_{train}$ has a one-to-one correspondence with an entry in y. The optimal θ is generally found by minimizing a loss function on $(X_{train}, y_{train})$ over possible values of θ. Mathematically, the minimization is given by:

$$\theta = \underset{\theta}{\mathrm{argmin}}\ \ell(X_{train}, y_{train}; \theta).$$

The batch gradient engine 312 returns a DP response 112 $\theta_{DP}$ of a differentially private batch gradient query by perturbing the loss function to be minimized. Specifically, the perturbed minimization is given by:

$$\theta_{DP} = \underset{\theta}{\mathrm{argmin}}\ \ell(X_{train}, y_{train}; \theta) + \theta^T v\left(G\left(\frac{4 \cdot K^2 \cdot R_2^2 \cdot \left(\log\frac{1}{\delta} + \epsilon\right)}{\epsilon^2}\right)\right),$$

in which K is the Lipschitz constant for loss function $\ell(\cdot)$. If j is the index of the columns in $X_{train}$, $x_i^j$ denotes the value of entry i and column j in $X_{train}$, and it is publicly known that for each column j, $a^j \leq x_i^j \leq b^j$, $R_2$ may be given by:

$$R_2 = \max(\|u\|_2 | a^j \leq u^i \leq b^j)$$

where u is a vector having elements $u^i$. The DP response 112 $\theta_{DP}$ may be provided for display on the user interface 150.

Stochastic Gradient Engine 314

Similarly to the batch gradient engine 312, the stochastic gradient engine 314 produces a DP response 112 responsive to the differentially private security system 102 receiving a valid query 108 for generating a set of parameters θ for a general linear model that captures the correlation between a series of observable features and a label feature, given privacy parameters (ε,δ). An example query command for accessing the stochastic gradient engine 314 is given in QC7 above.

Similar to the batch gradient engine 312, examples of general linear models supported by the stochastic gradient engine 314 are, but not limited to, linear regression, logistic regression, and support vector machine (SVM) classifiers.

The stochastic gradient engine 314 also minimizes a loss function on training data $(X_{train}, y_{train})$ over possible values of θ to find the optimal vales of parameter vector θ. However, the stochastic gradient engine 314 may minimize the loss function based on individual points or a subset of the training data, instead of the entire training data.

As discussed in reference to the batch gradient engine 312, a general minimization problem for finding the optimal values for θ over training data $(X_{train}, y_{train})$ is given by:

$$\theta = \underset{\theta}{\operatorname{argmin}} \, l(X_{train}, y_{train}; \theta)$$

where l(·) is a loss function. The minimization is solved by applying stochastic gradient descent on the loss function l(·) with respect to θ. This involves the steps of identifying an initial set of values for θ, calculating the gradient of the loss function with respect to θ, and updating θ based on the calculated gradient. The steps are repeated until the algorithm reaches convergence, and an optimal set of values for θ that minimize the loss function are identified.

Specifically, given the estimate for the parameter $\theta_t$ at time t, stochastic gradient descent generates a new estimate $\theta_{t+1}$ at the next time step t+1 by the following equation:

$$\theta_{t+1} = \theta_t - \eta_t \cdot n \cdot \nabla_{\theta_t} l(X_{train}, y_{train}; \theta),$$

in which $\nabla_{\theta_t} l(X_{train}, y_{train}; \theta)$ is the gradient of the loss function with respect to θ, and $\eta_t$ is the learning rate. The algorithm is repeated until the estimate for θ converges.

The stochastic gradient engine 314 returns a DP response 112 $\theta_{DP}$ of a differentially private stochastic gradient query by perturbing the update of θ at one or more time steps of the stochastic gradient descent algorithm. Specifically, a perturbed update at time t to t+1 is given by:

$$\theta_{t+1} = \theta_t - \eta_t \cdot n \cdot \nabla_{\theta_t} l(X_{train}, y_{train}; \theta) - \eta_t \cdot v\left(G\left(\frac{c_1^2 \cdot n^2 \cdot \left(\log\frac{n}{\delta} \cdot \log\frac{1}{\delta}\right)}{\epsilon^4}\right)\right),$$

where $\eta_t$ is the learning rate.

The stochastic gradient engine 314 may output the perturbed update at each time step as the DP response 112 for display on the user interface 150, or the converged parameter vector $\theta_{DP}$ as the DP response 112 for display on the user interface 150.

Random Forest Engine 316

In one embodiment, the random forest engine 316 produces a DP response 112 responsive to the differentially private security system 102 receiving a valid query 108 for generating a trained random forest classifier that bins a series of feature values into one among multiple categories, given privacy parameters (ε,δ). The random forest classifier is trained on the selected columns of X. An example query command for accessing the random forest engine 316 is given in QC8 above. For the example data object X shown in FIG. 2, the client 104 may submit a query 108 to return a DP response 112 for generating a trained random forest classifier that receives values for the height and age of a patient and determines whether the patient has contracted the disease or not.

The random forest classifier, is trained on training data $(X_{train}, y_{train})$ to learn the correlation between the selected features of an entry and the category the entry belongs to. Specifically, $X_{train}$ is a matrix database in which each column corresponds to a selected feature of interest to the client 104, and y is a column vector of already known labels indicating the category of a corresponding entry. Each entry in $X_{train}$ has a one-to-one correspondence with a label entry in y. Upon being trained, the random forest classifier, or a classifier in general, receives a new data entry with selected feature values and generates an estimate of the category for the new entry.

The random forest classifier is an ensemble of individual binary decision tree classifiers, in which each binary decision tree generates an estimate for the category of an entry. Given a new data entry, the random forest classifier aggregates the category estimates from each binary decision tree and produces a final estimate for the category of the data entry.

Figure 5:
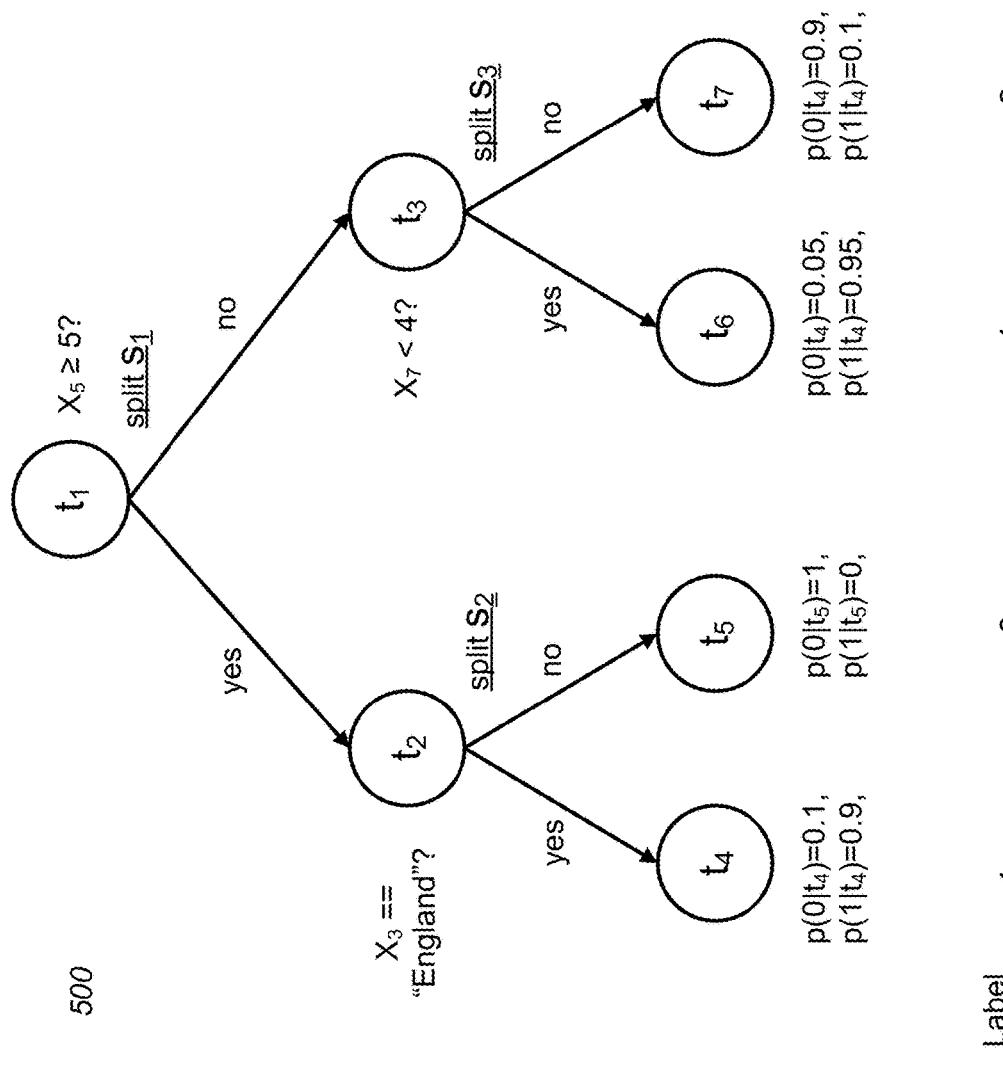
FIG. 5 illustrates an example binary decision tree for use in a differentially private random forest query, according to one embodiment.

FIG. 5 is an example diagram of a trained binary decision tree, according to one embodiment. Each decision tree includes a hierarchical structure with a plurality of T nodes $t_i$=1, 2, . . . , T and a plurality of directed edges between a parent node and a child node. A parent node is a node that has outgoing edges to a child node, and a child node is a node that receives edges from a parent node. In the particular embodiment of a binary decision tree, each parent node has two child nodes. The nodes may also be identified as a root node, in which the node has no incoming edges, an internal node, in which the node has one incoming edge with two outgoing edges, and a leaf node, in which the node has one incoming edge with no outgoing edges. For example, the example decision tree in FIG. 5 has seven nodes t1, t2, . . . , t7 and six edges. t1 is the root node, t2 and t3 are internal nodes, and t4-t7 are leaf nodes.

For each generated binary decision tree, each node except the root node corresponds to a partition of training data entries formed by a split s at a parent node. The split s at the parent node is based on a test condition of a feature of the training data $(X_{train}, y_{train})$ that compares the feature value of an entry to a reference value, and verifies whether the feature value meets that condition or not. The features may be selected from among random subsets of the features of the training data. Returning to the example shown in FIG. 5, node $t_1$ creates a split $s_1$ into two child nodes $t_2$ and $t_3$ based on the test condition $x_5 \geq 5$, which checks if an entry contains a fifth feature value equal to or greater than 5. The training data $(X_{train}, y_{train})$ is thus split at $s_1$ into one partition that contains entries with $x_{5 \geq 5}$, and another partition that contains entries with $x_5 < 5$. The former partition is directed to child node $t_1$ and the latter partition is directed to child node $t_2$. The partitioning process is repeated until the leaf nodes of the binary decision tree are determined.

At the end of the training process, each leaf node is associated with a category that has a dominant proportion in the corresponding partition at the leaf node. In FIG. 5, leaf node t4 is assigned label "1," since the proportion of "1" labels in leaf node t4, denoted by p(1|t4), is greater than the proportion of "0" labels in leaf node t4, denoted by p(0|t4). Given a new data entry with an unknown category, the trained decision tree generates a label estimate by checking the appropriate feature values of the data entry at each node as it propagates through the tree to a destination leaf node. Upon arriving at the leaf node, the data entry is assigned the category label associated with the leaf node.

The random forest engine 316 returns a DP response 112 of a differentially private random forest query by perturbing the proportion of training data entries at leaf nodes of each trained binary decision tree. Specifically, the random forest engine 316 trains a random forest classifier T with an ensemble of $N_{trees}$ binary decision trees $B_{j=1, 2, \ldots, Ntrees}$ using training data $(X_{train}, y_{train})$ from the data object X. Assuming a binary classification problem with two labels "0" and "1," the random forest engine 316 perturbs the proportion of data entries associated with each category for each leaf node $t_L$. The perturbed proportion $p_{DP}(\cdot|t_L)$ is given by:

$$p_{DP}(0|t_L) \approx p(0|t_L) + L\left(\frac{\epsilon}{\log N_{trees}}\right),$$

$$p_{DP}(1|t_L) \approx p(1|t_L) + L\left(\frac{\epsilon}{\log N_{trees}}\right).$$

The random forest engine 316 returns the random forest classifier $T_{DP}$ containing an ensemble of perturbed binary decision trees $B_{DPj=1, 2, \ldots, Ntrees}$ as the DP response 112. Moreover, the random forest engine 316 may display the perturbed proportion of data entries for leaf nodes of each binary decision tree $B_{DPj-1, 2, \ldots, Ntrees}$ for display on the user interface 150.

Histogram Engine 318

The histogram engine 318 produces a DP response 112 responsive to the differentially private security system 102 receiving a query 108 for generating a histogram of a selected column in X, given privacy parameters (ε,δ). The histogram engine 318 creates one or more bins corresponding to one or more disjoint ranges of the selected feature values, and indicates the number or proportion of entries that belong to each bin. An example query command for accessing the histogram engine 318 is given in QC9 above. For the example data object X shown in FIG. 2, the client 104 may submit a query 108 to return a DP response 112 for generating a histogram of the age of all patients for bins age 0-10, 11-20, 21-30, and so on.

The histogram engine 318 returns a DP response 112 of a differentially private histogram query by perturbing the counts for each bin.

Figure 6:
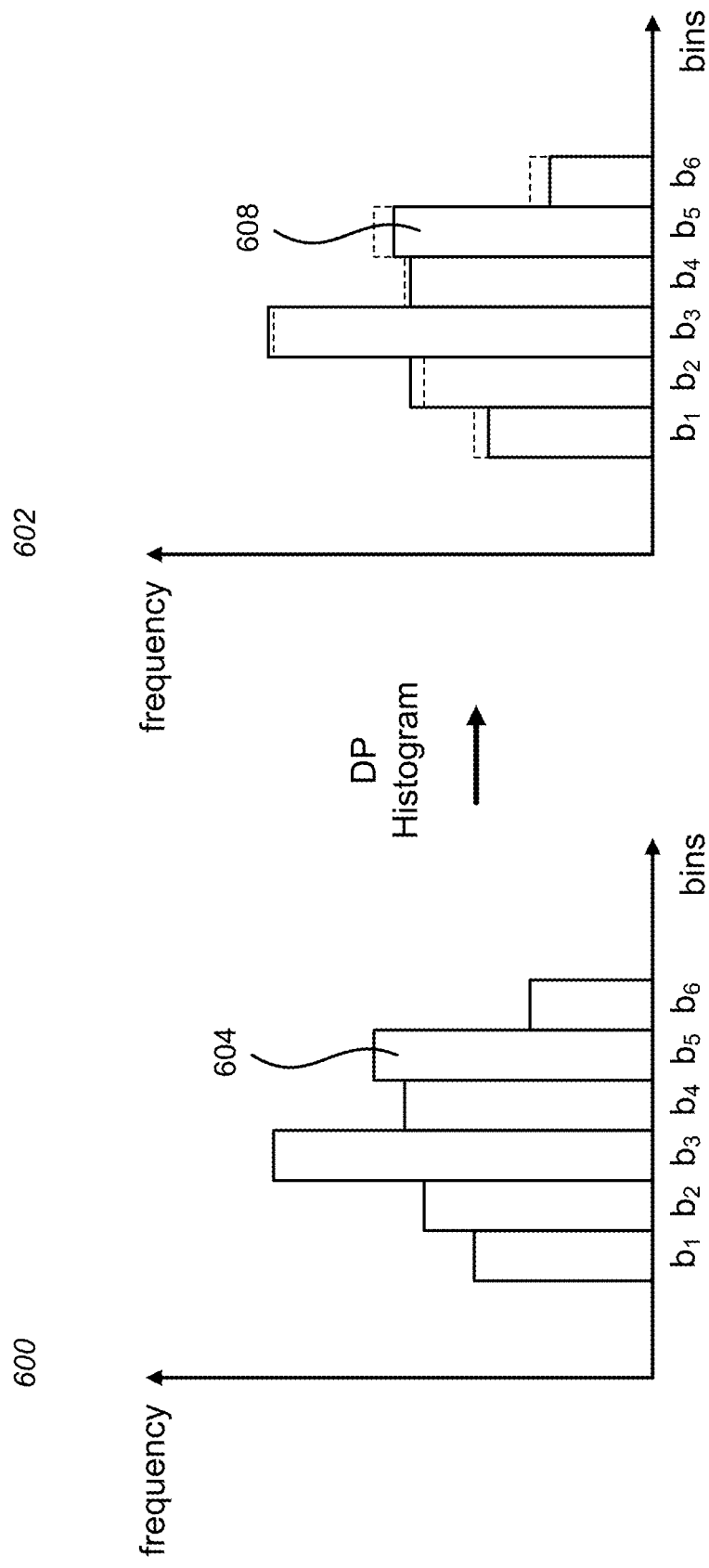
FIG. 6 illustrates perturbing the counts for a differentially private histogram query, according to one embodiment.

In one embodiment, the histogram engine 318 generates the requested histogram from the selected column of X, and perturbs the counts of each bin by submitting a request to the count engine 302. FIG. 6 illustrates perturbing the counts for a differentially private histogram query, according to one embodiment. As shown in FIG. 6, the histogram engine 318 generates histogram 600 by counting the number of entries corresponding to each bin $b_{i=1, 2, \ldots, B}$. The histogram engine 318 then requests the count engine 302 to perturb the counts qi for each bin to generate a perturbed histogram 602. As shown in FIG. 6, the count 608 for bin $b_5$ in the perturbed histogram 602 is a perturbed version of count 604 in the original histogram 600.

In another embodiment, the histogram engine 318 generates the requested histogram from the selected column of X, and perturbs the counts of each bin by decomposing the counts using a private wavelet decomposition algorithm. In such an embodiment, the histogram engine 318 aggregates the counts $q_{i=1, 2, \ldots, B}$ for each bin $b_{i=1, 2, \ldots, B}$ into a matrix (or vector) Q. The histogram engine 318 decomposes Q into a tree structure that is representative of a wavelet decomposition. Each leaf node of the tree corresponds to a count $q_i$, and each parent node of the tree corresponds to one of multiple wavelet coefficients $c_{j=1, 2, \ldots, m}$. The value of a wavelet coefficient $c_j$ is calculated based on the counts $q_i$ incorporated in the leaf nodes of the tree. This allows a count $q_i$ to be reconstructed as a function $f_i$ of the wavelet coefficients $c_{j=1, 2, \ldots, m}$. That is, for each count $q_i$:

$$q_i = f_i(c_0, c_1, \ldots, c_m).$$

The histogram engine 318 generates a perturbed histogram by perturbing the wavelet coefficients, and reconstructing the counts using the perturbed wavelet coefficients. Specifically, the perturbed wavelet coefficients $c^{DP}_{i=1, 2, \ldots, m}$ are given by:

$$c_i^{DP} = c_i + L\left(\frac{2^{l+1}}{\epsilon \cdot m}\right).$$

The reconstructed counts from the perturbed wavelet coefficients is now given by:

$$q_i^{DP} = f_i(c_0^{DP}, c_1^{DP}, \ldots, c_m^{DP}).$$

The histogram engine 318 outputs the perturbed histogram as the DP response 112 for display on the user interface 150.

In one embodiment, the histogram engine 318 may also be used to generate a differentially private visualization of data entries as described above in reference to the count engine 302 and FIG. 4. For example, the histogram module 318 may construct a multi-dimensional histogram corresponding to counts of the requested data entries in each region, perturb the histogram using mechanisms described above (e.g., private wavelet decomposition algorithm), and display the differentially private plot of the requested data entries on the user interface 150.

Model Testing Engine 320

The model testing engine 320 produces a DP response 112 responsive to the differentially private security system 102 receiving a query 108 for testing the performance of a classification model, given privacy parameters (ε,δ). The classification model is trained and tested on selected columns of X. As such, the model testing engine 320 may be appended to any other module that trains a classifier on X, such as the batch gradient engine 312, the stochastic gradient engine 314, or the random forest engine 316. For the example data object X shown in FIG. 2, the client 104 may submit a query 108 to return a DP response 112 for generating a performance evaluation of a support vector machine classifier that was trained using the stochastic gradient engine 314.

As discussed in reference to the random forest engine 316, classification models in general is trained on training data $(X_{train}, y_{train})$ to learn the correlation between selected features of an entry and the category the entry belongs to. The training data $(X_{train}, y_{train})$ may be extracted from a subset of entries contained in the data object X. Upon being trained, the classifier is able to receive a new data entry containing values for the selected features and generate an estimate of the category for the new entry.

Often times, the estimate of the category for an entry is determined by applying a cutoff threshold to a numerical, not categorical, output of a classifier. For example, in the random forest classifier described in reference to the random forest engine 316, the category associated with a leaf node $t_L$ is determined by the proportion of training data entries associated with each category, which is a numerical value. The random forest engine 316 may determine that a leaf node is associated with category "0" if the proportion of entries associated with label "0" is above a cutoff threshold of 0.5, 0.6, or 0.7. As another example, logistic regression classifiers output a numerical value in the range of [0, 1] given an entry of feature values. The entry may be classified into category "0" if the associated output is below a cutoff threshold of 0.5, 0.4, or 0.3. Regardless of the example, the cutoff threshold for determining the boundary between each category is a critical parameter depending on the context the classifier is applied to.

The model testing engine 320 receives a trained classifier and tests the performance of the trained classifier a series of cutoff thresholds, and generates a confusion matrix for each threshold indicating the performance of the classifier. The model testing engine 320 may test the performance of the classifier on testing data ($X_{test}$, $y_{test}$). Similarly to training data, $X_{test}$ contains a set of entries with selected feature values, and $y_{test}$ contains a vector of already known labels for each corresponding entry in $X_{test}$. However, in contrast to training data, testing data ($X_{test}$, $y_{test}$) comprises entries that are not present in training data ($X_{train}$, $y_{train}$). That is, testing data comprises entries that the classifier has not "seen" yet.

Figures 7A, 7B:
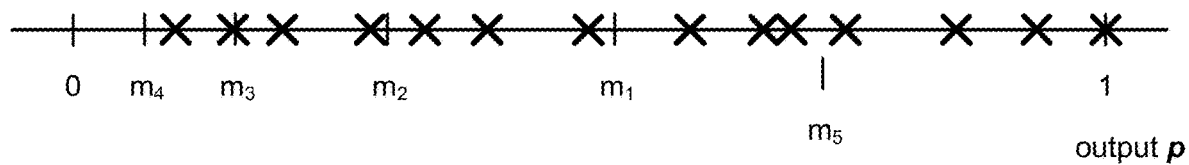
FIG. 7A illustrates a recursive process for identifying threshold points of the classification output vector for a differentially private model testing query, according to one embodiment.
FIG. 7B illustrates an example confusion matrix generated during a differentially private model testing query.

The model testing engine 320 generates a series of cutoff thresholds based on the numerical values of p. FIG. 7A illustrates a recursive process for identifying threshold points of the classification output vector for the model testing engine 320, according to one embodiment. As shown in FIG. 7A, sample values of p are plotted on a range of 0 to 1. A series of k cutoff thresholds, or a series of intervals, are recursively identified by the median engine 304 such that the number of elements of p in each interval is approximately equal. Specifically, the median engine 304 recursively identifies the perturbed median for an interval and subsequently, its corresponding sub-intervals generated by dividing the interval by the identified perturbed median, until k thresholds are identified.

For example, as shown in FIG. 7, the median engine 304 identifies $m_1$ as the perturbed median for the first interval [0, 1]. Subsequently, the median engine 304 identifies $m_2$ as the perturbed median for the resulting sub-interval [0, $m_1$], and $m_5$ as the perturbed median for the sub-interval [$m_1$, 1]. This process is repeated for sub-intervals [0, $m_2$], [$m_2$, $m_1$], [$m_1$, $m_5$], [$m_5$, 1] and for its sub-intervals until k thresholds, $m_i$=1, 2, . . . , k are identified.

For each threshold $m_i$, the model testing engine 320 generates corresponding category label estimates from p, and compares the estimates to the vector of known labels $y_{test}$. Given the comparisons, the model testing engine 320, constructs a confusion matrix that evaluates the performance of the classifier.

FIG. 7B illustrates an example confusion matrix 700 generated by the model testing engine 320, according to one embodiment. As shown in FIG. 7B, the confusion matrix 700 contains the number of testing data entries for 4 categories: i) entries that have an actual category of "1" and an estimate category of "1" ("True Positive" entries), ii) entries that have an actual category of "0" and an estimate category of "0" ("True Negative" entries), iii) entries that have an actual category of "0" and an estimate category of "1" ("False Positive" entries), and iv) entries that have an actual category of "1" and an estimate category of "0" ("False Negative" entries). For a given threshold, a data entry only contributes to one among the 4 categories.

For each threshold $m_i$, the model testing engine 320 generates a perturbed confusion matrix by using the histogram engine 318. This is because each entry contributes to only one among the 4 disjoint categories, and thus, the entries in the confusion matrix 700 can be viewed as a histogram. The model testing engine 320 outputs each threshold $m_i$, and the corresponding perturbed confusion matrix as the DP response 112 for display on the user interface 150.

Synthetic Database Engine 322

The synthetic database engine 322 produces a DP response 112 responsive to the differentially private security system 102 receiving a query 108 for transforming X into a synthetic database S, given privacy parameters ($\varepsilon,\delta$). The resulting synthetic database S has a number of entries corresponding to that in X, but a fewer number of columns or features than X. Moreover, the spatial relationship between a pair of entries in X is retained in S. The transformation of X to S is ($\varepsilon,\delta$)-differentially private with respect to a neighboring data object X' with a 1-element difference from X.

The synthetic database engine 322 produces a DP response 112 of a differentially private synthetic database query by projecting the elements of X to S using a projection matrix. Assuming that data object X is a n×p matrix having n rows and p columns, the transformation by the synthetic database engine 322 is given by:

$$S = X * J\left(G\left(\frac{4 \cdot \log \delta}{n^2 \cdot \epsilon^2}\right)\right)$$

where J is a p×k projection matrix, with k<p. The resulting synthetic database matrix S is a n×k matrix containing equal number of entries or rows as data object matrix X, but containing a smaller number of features or columns than the original data object X.

As discussed above, the transformation using projection matrix J is ($\varepsilon,\delta$)-differentially private. Moreover, the spatial relationship between a pair of entries in X is retained in S. That is, the distance between a pair of entries ($x_i,x_j$) in the p-dimensional feature space of X is approximately equal to the distance between a pair of entries ($s_i,s_j$) in the k-dimensional feature space of S. The synthetic database engine 322 outputs S as the DP response 112 for display on the user interface 150.

Figure 8:
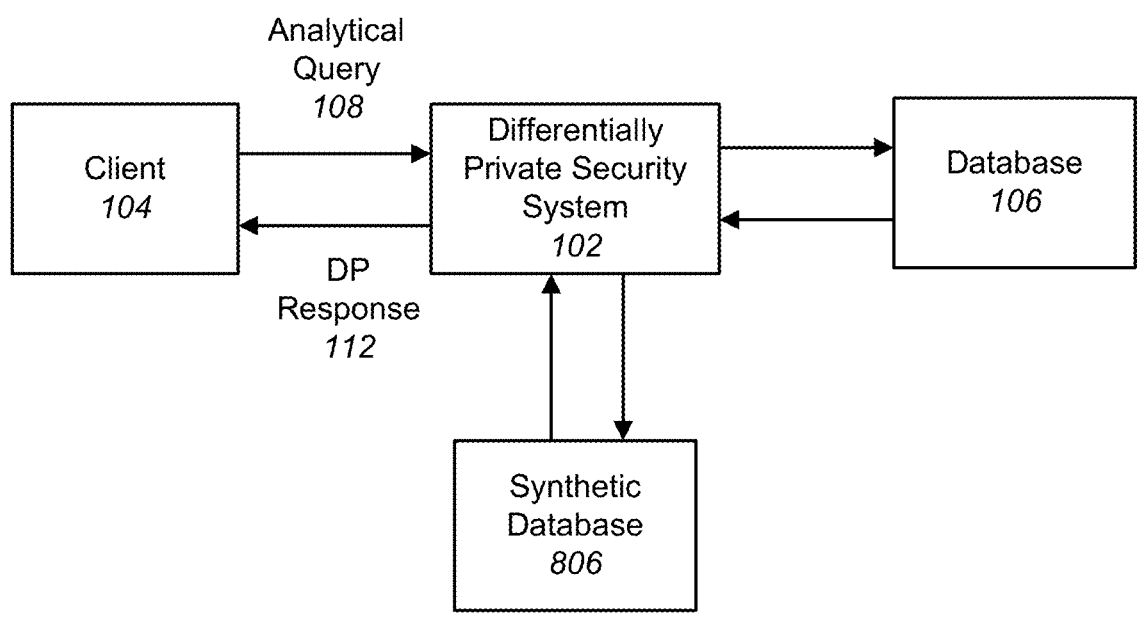
FIG. 8 illustrates a system-level modification to the system of FIG. 1 that allows the client to access to a differentially private synthetic database, according to one embodiment.

FIG. 8 is a modification 800 of the system 100 in FIG. 1 that allows the client 104 access to synthetic database 806 generated by the synthetic database engine 322, according to one embodiment. As shown in FIG. 8, the modified system 800 may allow the client 104 to access the synthetic database 806 generated by the synthetic database engine 322 through the differentially private security system 102. Since the transformation from X to S is ($\varepsilon,\delta$)-differentially private, the privacy of X is retained.

Figure 9:
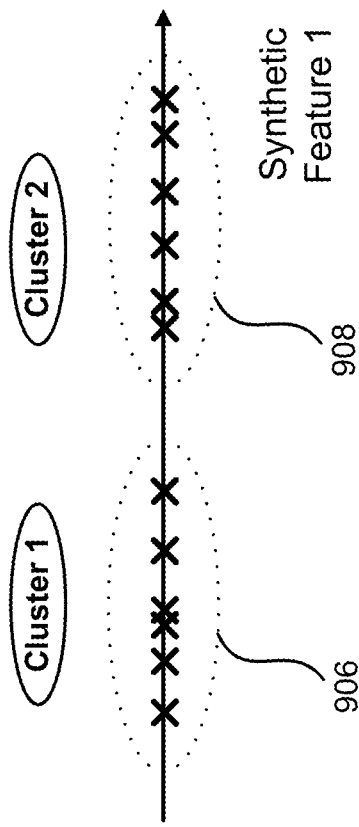
FIG. 9 illustrates the application of a clustering query to entries of a differentially private synthetic database, according to one embodiment.
Figure 9:
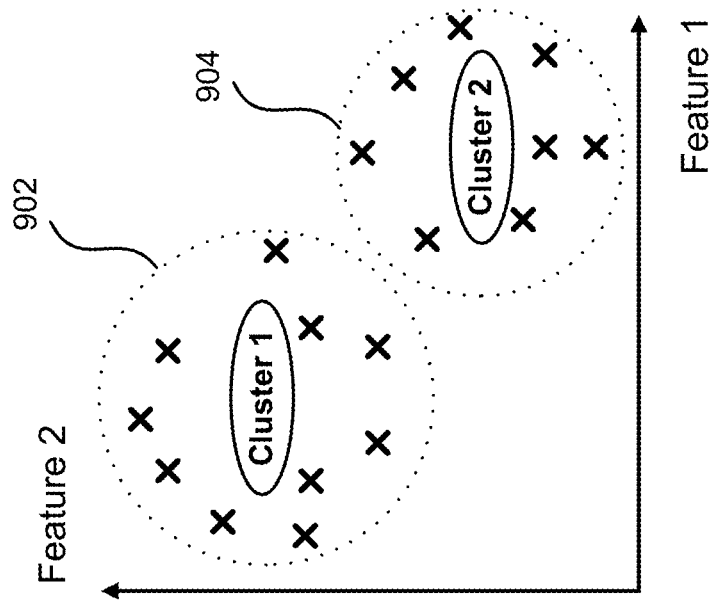

FIG. 9 illustrates applying a clustering query to entries of the synthetic database, according to one embodiment. The various modules of the privacy system 160 and other analytical modules may be applied to the synthetic database 806 instead of the data object X to extract patterns or trends related to the information in X. The results of the analysis on the synthetic database 806 may also be provided for display on the user interface 150. For example, the client 104 may submit a clustering query on the entries of the synthetic database 806 using the batch gradient engine 312 or the stochastic gradient engine 314.

In the example of FIG. 9, clusters 902 and 904 are results of a non-differentially private clustering query on a data object X having two columns or features. Each cluster 902 and 904 are associated with a group of entries. Since the clustering query is not differentially private on X, the results of the query are not shown to the client 104. Clusters 906 and 908 are results of a non-differentially private clustering query on the synthetic database S having one column or feature due to the transformation by the synthetic database engine 322. Since the transformation preserves the spatial relationship between a pair of entries, cluster 906 is largely associated with the same entries in cluster 902, and cluster 908 is largely associated with the same entries in cluster 904. Since the synthetic database S is $(\varepsilon,\delta)$-differentially private, the results of the clustering query may be displayed to the client 104 using the user interface 150.

Validation Engine 324

The validation engine 324 produces a DP response 112 responsive to the differentially private security system 102 receiving a request for whether a query 108 satisfies the definition of $(\varepsilon,\delta)$-differential privacy for privacy parameters $(\varepsilon,\delta)$. In one embodiment, the validation engine 324 may receive a function call from the client 104 that points to the query 108. The query 108 may be, for example, an analytical model or an algorithm that can be applied to a data object X.

The validation engine 324 certifies whether the received query 108 satisfies the definition of $(\varepsilon,\delta)$-differential privacy by applying the query 108 to example pairs of neighboring data objects (Z, Z'). Specifically, the validation engine 324 generates pairs of neighboring data objects (Z, Z'), having at most 1 entry different from each other. The validation engine 324 applies the received query 108 to each example pair of neighboring data objects (Z, Z') and determines whether an estimate of the quantity $Pr[M(X) \in S]/Pr[M(X') \in S]$ satisfies the definition of $(\varepsilon,\delta)$-differential privacy over a sampling of outputs from S of the query M and over the randomness of the query M.

In one embodiment, the validation engine 324 may output a binary value to the client 104 as the DP response 112 for display on the user interface 150 that indicates whether or not the query 108 is $(\varepsilon,\delta)$-differentially private. In some embodiments, the validation engine 324, in response to a determination that the query 108 is not $(\varepsilon,\delta)$-differentially private, can reject or deny the query.

Figure 10:
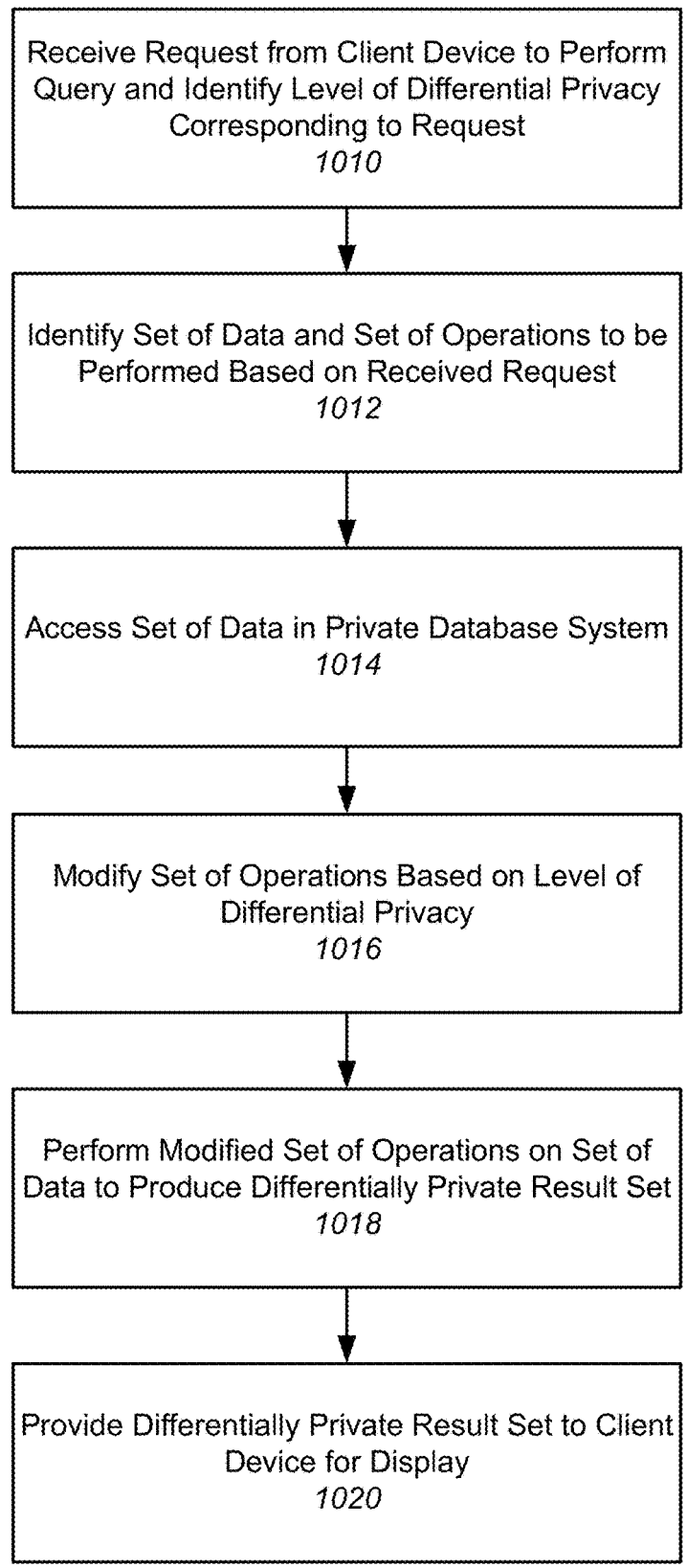
FIG. 10 illustrates a process for responding to a database query by executing a differentially private version of the query on the database, according to one embodiment.

FIG. 10 illustrates a process for responding to a database query by executing a differentially private version of the query on the database, according to one embodiment. Different embodiments can perform additional and/or different steps. Furthermore, other embodiments can perform the steps in different orders.

A request from a client 104 to perform a query is received 1010 and a level of differential privacy corresponding to the request is identified. A set of data in the private database system and a set of operations to be performed based on the received request is identified 1012. The set of identified data in the private database system is accessed 1014. The set of operations is modified 1016 based on the received level of differential privacy. The set of modified operations is performed 1018 on the set of data to produce a differentially private result set. The differentially private result set is provided 1020 to the client 104 for display on the client.

Figure 11:
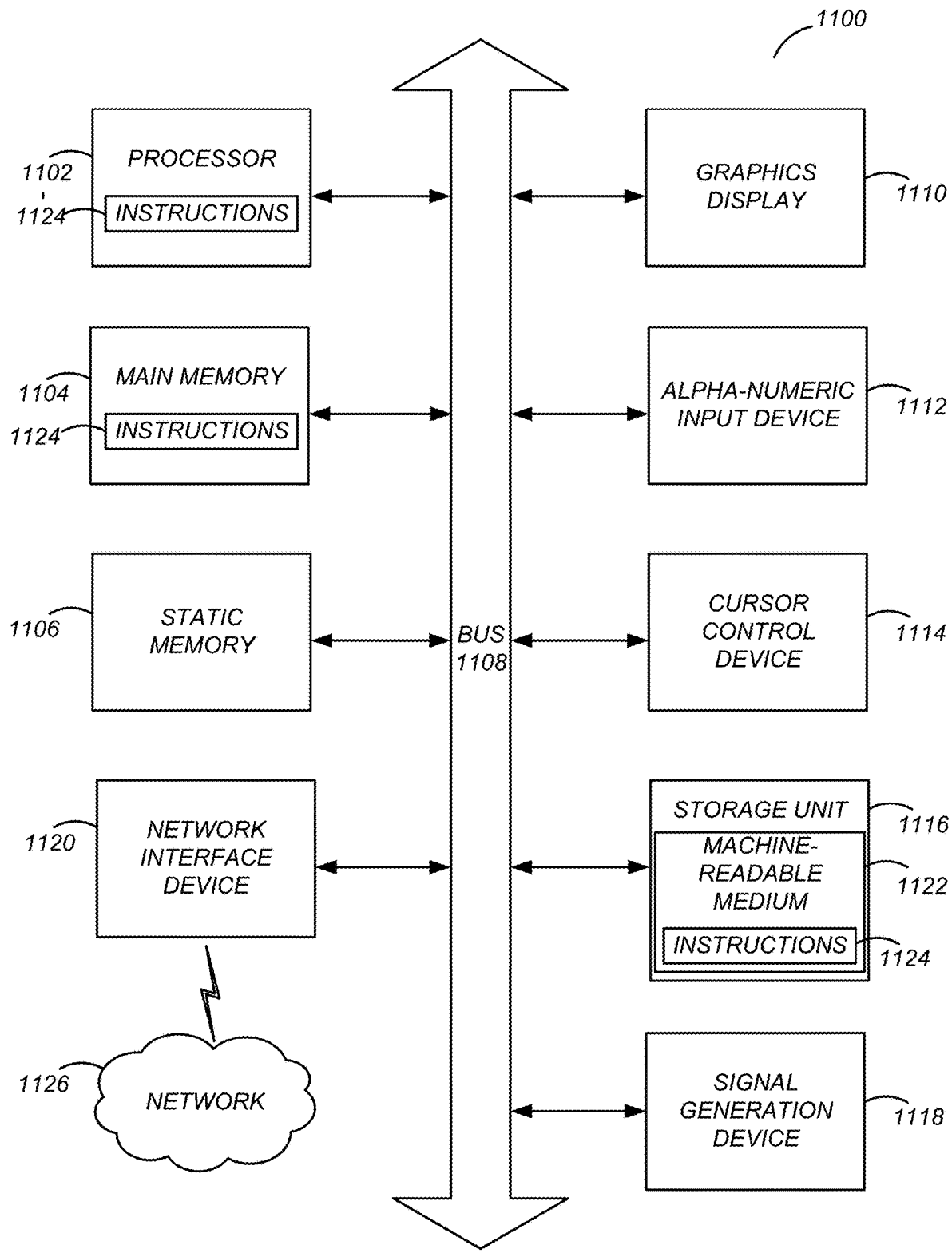
FIG. 11 is a block diagram illustrating components of an example machine able to read instructions from a machine-readable medium and execute them in a processor (or controller).

FIG. 11 is a block diagram illustrating components of an example machine able to read instructions from a machine-readable medium and execute them in a processor (or controller). Specifically, FIG. 11 shows a diagrammatic representation of a machine in the example form of a computer system 1100. The computer system 1100 can be used to execute instructions 1124 (e.g., program code or software) for causing the machine to perform any one or more of the methodologies (or processes) described herein. In alternative embodiments, the machine operates as a standalone device or a connected (e.g., networked) device that connects to other machines. In a networked deployment, the machine may operate in the capacity of a server machine or a client machine in a server-client network environment, or as a peer machine in a peer-to-peer (or distributed) network environment.

The machine may be a server computer, a client computer, a personal computer (PC), a tablet PC, a set-top box (STB), a smartphone, an internet of things (IoT) appliance, a network router, switch or bridge, or any machine capable of executing instructions 1124 (sequential or otherwise) that specify actions to be taken by that machine. Further, while only a single machine is illustrated, the term "machine" shall also be taken to include any collection of machines that individually or jointly execute instructions 1124 to perform any one or more of the methodologies discussed herein.

The example computer system 1100 includes one or more processing units (generally processor 1102). The processor 1102 is, for example, a central processing unit (CPU), a graphics processing unit (GPU), a digital signal processor (DSP), a controller, a state machine, one or more application specific integrated circuits (ASICs), one or more radio-frequency integrated circuits (RFICs), or any combination of these. The computer system 1100 also includes a main memory 1104. The computer system may include a storage unit 1116. The processor 1102, memory 1104 and the storage unit 1116 communicate via a bus 1108.

In addition, the computer system 1106 can include a static memory 1106, a display driver 1110 (e.g., to drive a plasma display panel (PDP), a liquid crystal display (LCD), or a projector). The computer system 1100 may also include alphanumeric input device 1112 (e.g., a keyboard), a cursor control device 1114 (e.g., a mouse, a trackball, a joystick, a motion sensor, or other pointing instrument), a signal generation device 1118 (e.g., a speaker), and a network interface device 1120, which also are configured to communicate via the bus 1108.

The storage unit 1116 includes a machine-readable medium 1122 on which is stored instructions 1124 (e.g., software) embodying any one or more of the methodologies or functions described herein. The instructions 1124 may also reside, completely or at least partially, within the main memory 1104 or within the processor 1102 (e.g., within a processor's cache memory) during execution thereof by the computer system 1100, the main memory 1104 and the processor 1102 also constituting machine-readable media. The instructions 1124 may be transmitted or received over a network 1126 via the network interface device 1120.

While machine-readable medium 1122 is shown in an example embodiment to be a single medium, the term "machine-readable medium" should be taken to include a single medium or multiple media (e.g., a centralized or distributed database, or associated caches and servers) able to store the instructions 1124. The term "machine-readable medium" shall also be taken to include any medium that is capable of storing instructions 1124 for execution by the machine and that cause the machine to perform any one or more of the methodologies disclosed herein. The term "machine-readable medium" includes, but not be limited to, data repositories in the form of solid-state memories, optical media, and magnetic media.

Random Forest Engine 316

Return now to the random forest engine 316 illustrated in the privacy system 160 of FIG. 3. As mentioned above, the random forest engine 316 produces a DP response 112 responsive to the differentially private security system 102 receiving a valid query 108 for generating a trained random forest classifier that bins a series of feature values into one category of multiple categories, given privacy parameters ($\varepsilon,\delta$). The discussion below provides additional details of how embodiments of the random forest engine 316 build a random forest classifier in a differentially private manner.

Figures 12A, 12B:
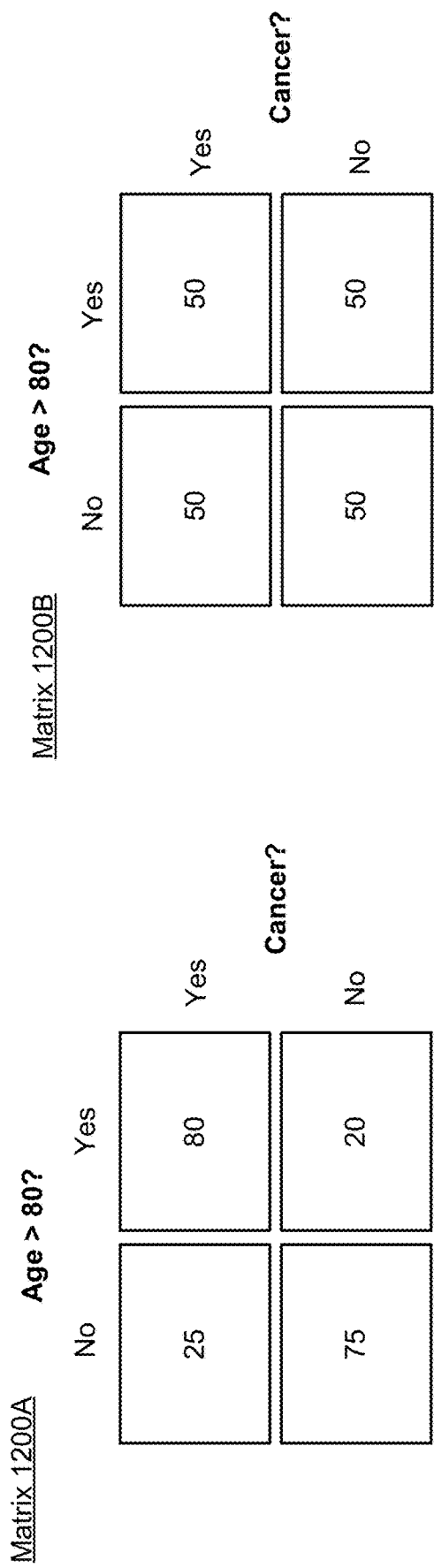
FIGS. 12A and 12B are diagrams illustrating the concept of information gain, according to one embodiment.

An understanding of information gain is useful for understanding the operation of the random forest engine 316. FIGS. 12A and 12B are diagrams illustrating the concept of information gain, according to one embodiment. Information gain is a measure of the relevance of a feature—a feature's correlation with an output. High information gain means a feature is correlated with an output and is therefore likely to be an accurate predictor for the correlated output. Conversely, low information gain means a feature is not correlated with an output and is therefore a poor predictor for the output.

For example, FIGS. 12A and 12B collectively show a pair of matrices 1200A, 1200B, each sorting a set of 200 people according to two criteria: whether the person is older than 80, and whether the person has cancer. Matrix 1200A indicates 25 of the 200 people are no older than 80 and have cancer, 80 are over 80 years of age and have cancer, 75 are no older than 80 and do not have cancer, and 20 are over 80 years of age and do not have cancer. If a cancer diagnosis is the output, matrix 1200A indicates a high correlation between age and cancer. Therefore a split (as described with reference to the random forest engine 316) at "Age >80" would provide significant information gain to a decision tree, such as a binary decision tree, when the tree is used to classify whether a person is likely to have cancer.

In contrast to matrix 1200A, matrix 1200B shows that each quadrant of the matrix includes exactly 50 people. Matrix 1200B thus provides no information gain because there are no trends in the data. Rather, the set of 200 people is distributed evenly among the bins. In such a scenario, adding a split at "Age >80" almost certainly does not improve the decision tree's ability to predict whether or not a person has cancer.

Splits in a trained binary decision tree are based on training data, as described in the earlier discussion of the random forest engine 316. Training data is not necessarily indicative of successful future classification, however. One set of training data may result in matrix 1200A and another may result in matrix 1200B. Even if all people in the set of 200 people over 80 years of age had cancer and all people 80 years or younger did not have cancer, another person not in the set could be over 80 and not have cancer, or be under 80 and have cancer. This is a reason why, as detailed above, the random forest classifier is an ensemble of individual decision tree classifiers, in which each decision tree generates an estimate for the category of an entry. Training data may indicate significant information gain when there is in reality none, or conversely may indicate no information gain when in reality there is a definite trend. As each decision tree is trained separately, each will have its own splits, the combination of decision trees forming a random forest classifier will dampen the effects of wrongfully determined information gain at any one decision tree.

Figure 13:
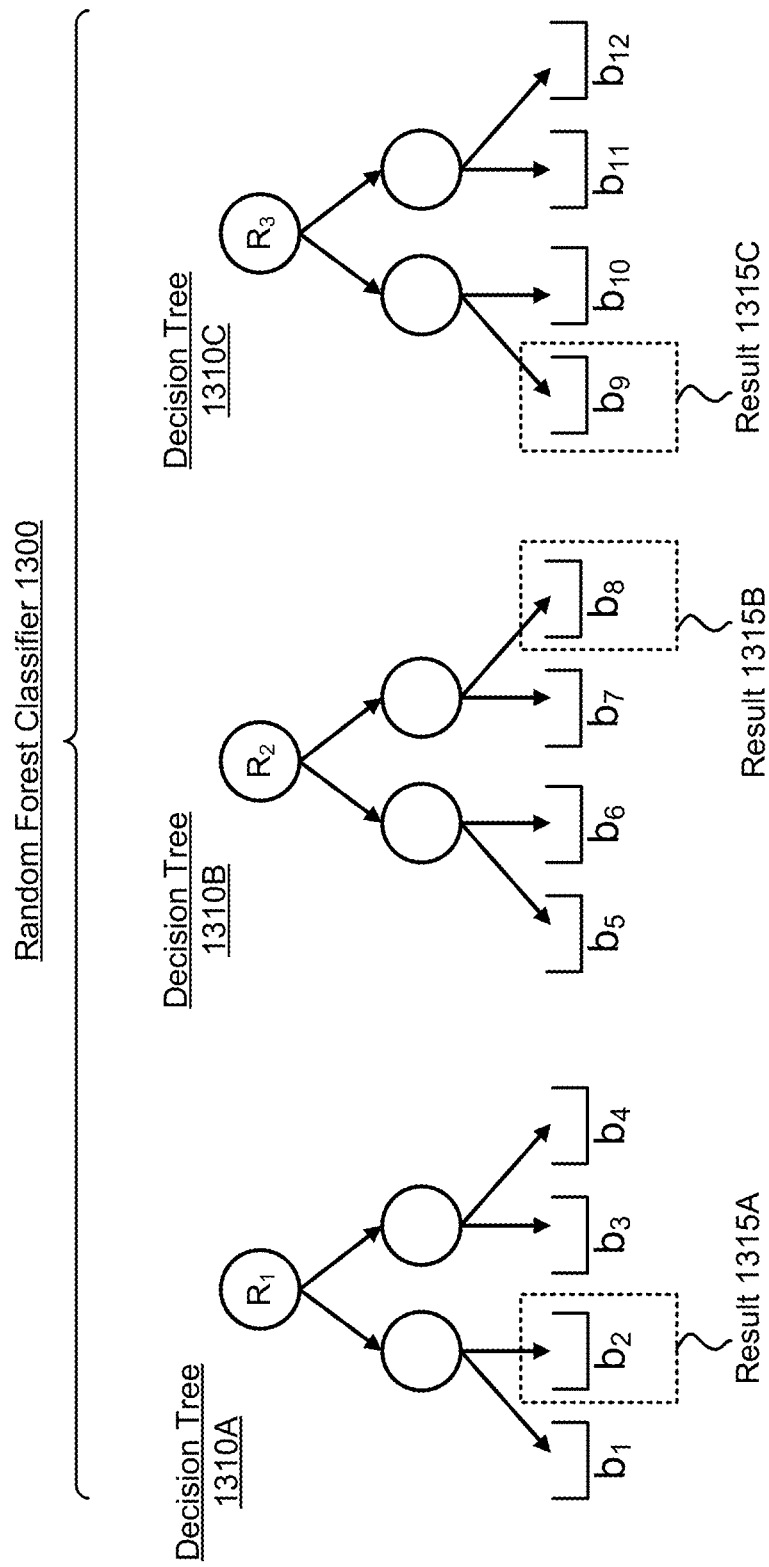
FIG. 13 illustrates a random forest classifier comprised of three decision trees, according to one embodiment.

FIG. 13 illustrates a random forest classifier 1300 comprised of three decision trees 1310A-C, according to one embodiment. Each decision tree 1310 includes a root node ($R_{1-3}$), two internal nodes, and four leaf nodes ($b_{1-4}$, $b_{5-8}$, and $b_{9-12}$, respectively). Each decision tree 1310 is trained for a set of categorical variables and each leaf node is associated with a count for a category, e.g. a count for how many data points in the training data reach the leaf node and are classified as "0" and a count for how many data points in the training data reach the leaf node and are classified as "1" respectively. In an embodiment, each leaf node is instead labeled with a category label, e.g. either with category label "0" or category label "1," based on the counts. For example, for each categorical variable, each leaf node is associated with a category label based on which category is associated with the greater count. An entry classified using the random forest classifier 1300 is classified as either "0" or "1" depending upon which label a majority of the decision trees determine for the entry (either 2 or 3 decision trees in this example).

Alternatively, an entry classified using the random forest classifier 1300 produces a probability that the entry is one or more classification options based on the counts at each leaf node reached by the entry. For example, if the entry reaches leaf nodes $b_2$, $b_8$, and $b_9$ as illustrated in FIG. 13, the entry's classification can depend upon the relative count of each classification option at each of those three leaf nodes and at the other leaf nodes associated with the same splits, leaf nodes $b_1$, $b_7$, and $b_{10}$. If $b_2$ has a count of 10 for option "0" (versus a count of 5 for option "1" in $b_1$) $b_8$ has a count of 5 for option "0" (versus a count of 1 for option "1" in $b_7$) and $b_9$ has a count of 30 for option "0" (versus a count of 35 for option "1" in $b_{10}$) the aggregate of each count may be determined and the resultant ratio may be the resultant probability, the classification. In this example, the aggregate count for "0" is 45 (from the sum of the counts of $b_2$, $b_8$, and $b_9$) and the aggregate count for "1" is 41 (from the sum of the counts of $b_1$, $b_7$, $b_{10}$). As such, the resultant probability, the classification, may be 46:41 odds (or approximately a 52.9% probability) that the entry is classified as "0." Depending upon the embodiment, one or more other classification techniques may instead or additionally be employed.

As an example of an entry traversing a tree, an entry E traverses each tree according to its features, first at a split at the root and then at one of the two internal nodes depending upon its features in relation to each split. Eventually, E's traversal ends at one of four leaf nodes, depending upon its features in relation to the split at the internal node (which it reached as a result of the first split). Traversal of decision tree 1310A categorizes E at $b_2$ and therefore result 1315A, the label "0." Similarly, traversal of decision tree 1310B for E leads to result 1315B, the label "0" at $b_8$, and traversal of decision tree 1310C for E leads to result 1315C, the label "1" at $b_9$. Two of the labels are "0" and one is "1" meaning a majority of the labels are "0" and hence E is classified as "0" by the random forest classifier 1300. As mentioned above, in other embodiments count-based classification techniques may be used, which may produce a probability for a particular classification rather than a binary selection of one or the other.

Figure 14A:
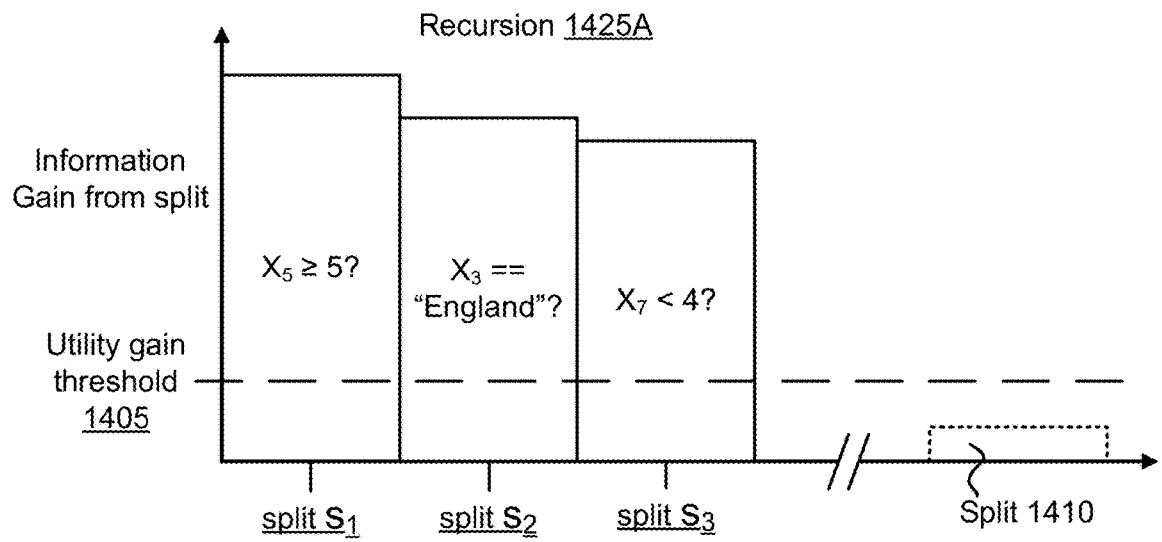
FIG. 14A is a diagram illustrating the concept of sorted information gain, according to one embodiment.
Figure 14B:
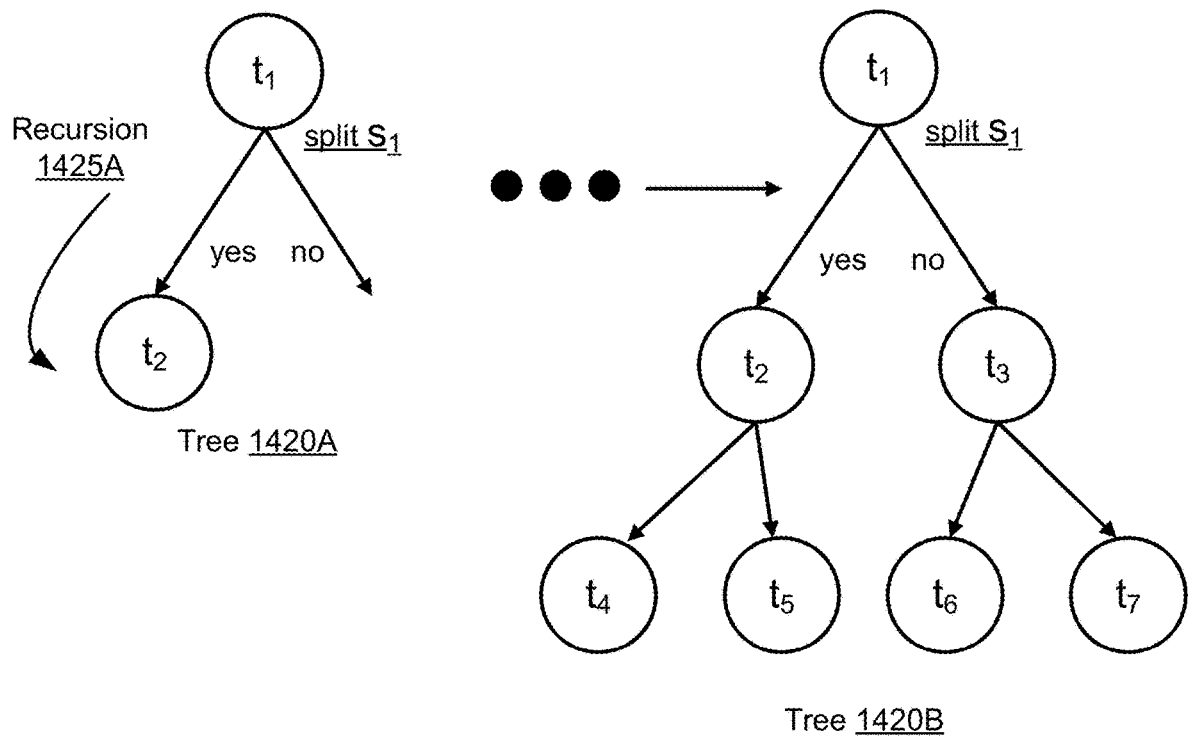
FIG. 14B illustrates recursive binary decision tree generation, according to one embodiment.

FIG. 14A is a diagram illustrating the concept of sorted information gain, according to one embodiment. FIG. 14B, in turn, illustrates recursive binary decision tree generation, according to one embodiment. Together the two figures illustrate recursive generation of a binary decision tree using information gain, according to one embodiment.

FIG. 14A includes a graph of splits from a set of splits determined from training data, sorted by information gain, and projected onto the y-axis. The splits may be based on random subsets of features of the training data. Split $S_1$ has the highest information gain and as such is sorted first. Next is split $S_2$ with the second highest information gain, then split $S_3$ with the third highest information gain, continuing until split 1410 with the least information gain of the set of splits.

The graph of FIG. 14A also illustrates the utility gain threshold 1405. This threshold 1405 is the amount of information gain at or below which a split with such an information gain is considered to be unusable for decision tree construction. For example, split 1410 would not be used as a split because its information gain is below the utility gain threshold—the utility gained from use of split 1410 in a decision tree is below an acceptable amount. The utility gain threshold 1405 may be set by a user of the differentially private security system 102 or may be determined based on the relative information gain of each split in the set of splits. For example, the utility gain threshold may be a certain percentile of information gain for the set of splits, or may be a certain number of standard deviations away from the mean of the information gain.

The set of splits may be recalculated or regenerated after each selection of a split based on a subset of remaining training data. For example, a training data set includes three data points. Data points A and B include categorical variables (e.g., columns) 1 and 2 and data point C includes categorical variables 2 and 3. If a split involving column 1 is selected, only data points A and B are used from that split on for that path in the decision tree. As such, after each split, only a subset of the overall training data set may be used. As such, in some embodiments different leaf nodes will have significantly different counts for each category, depending upon the extent to which the training data set was trimmed as a result of traversing the decision tree to the leaf node. For example, a first split may have leaf nodes with a count of 1,000 for category "0" and a count of 250 for category "1," while a second split may have leaf nodes with a count of 10 for category "0" and a count of 5 for category "1." Such discrepancies in the number of training data counted at each leaf node may be factored when classifying an entry.

FIG. 14B illustrates construction of a binary decision tree using the set of splits graphed in FIG. 14A. Generally, the tree is constructed by selecting an initial split to serve as the root node, and then recursively selecting additional splits to serve as children of previously selected nodes until a stopping condition is reached. The process continues until either the tree is recursively constructed to an intended size, e.g. a certain number of nodes or a certain depth, or until there are no more splits in the set of splits with an information gain above the utility gain threshold 1405.

In FIG. 14B, tree 1420A demonstrates that split $S_1$ is selected as the root node $t_1$, and the split for the "yes" condition branching from $t_1$ (represented by node $t_2$) is recursively selected 1425A. The recursion would continue to select a split for the "no" condition branching from $t_1$, for a node $t_3$, and then for the children of nodes $t_2$ and $t_3$, and so on. Tree 1420B illustrates the growth of tree 1420A after additional nodes are selected. In the latter tree 1420B, a split is selected for node $t_2$ and a split is selected for node $t_3$. Additional nodes $b_{13}$-$b_{16}$ are also shown. Nodes $b_{13-16}$ are the leaf nodes for tree 1420B, each containing the counts of either "yes" ($b_{13}$ and $b_{15}$) or "no" ($b_{14}$ and $b_{16}$) for a respective parent node's split.

Generally, each split is selected for a node based at least in part on the information gain provided by the split. If differential privacy is not applied to the random forest classifier, the splits selected for the nodes of the binary decision tree may be selected in descending order of information gain as determined for the set or subset of training data pertaining to each node. Thus, in the example of FIGS. 14A-B, $S_1$ would be chosen as the split for the root node. Then, as the tree 1420A is recursively constructed, a second split is selected at the next recursion 1425A (having the highest information gain for the subset of training data resulting from the split), and placed at the next node in the tree (node $t_2$), and so on for additional nodes and splits. Though not illustrated in the figure for purposes of clarity, tree construction finishes with the addition of leaf nodes for binning training data.

When splits are selected in this manner, however, an adversary may be able to derive at least some of the information within the training data based on an analysis of the splits in the binary decision tree. In particular, an adversary armed with information including the feature differentiated by the split and the relative information gain provided by the split may be able to ascertain features of particular entries in the training data. For example, the adversary may be able to determine whether a particular entry in the training data possesses a particular condition. This potential leakage of information is undesirable, particularly when the training data includes restricted data. As a result, use of databases to support analytical queries on restricted data in order to ascertain whether an entry has a particular condition, and particularly queries that involve construction and use of machine-learned models such as random forest classifiers, is impeded.

This issue is overcome by using a differentially private mechanism to select the splits for the nodes of the binary decision trees forming the random forest classifier. Rather than selecting the splits in descending order of information gain, an exponential mechanism uses the information gain of each split as a score for the quality function for that split. The splits for a binary decision tree are then selected responsive to evaluation of the exponential mechanism using the splits' respective scores. In other words, the quality function of the exponential mechanism is used in place of the direct information gain to select the split associated with a given node of the binary decision tree.

The exponential mechanism maps a set of n inputs from domain D to a range R. The mapping may be randomized, in which case each element of the domain D corresponds to the probability distribution over the range R. The mechanism selects a result r from the range R biased by the quality function. The quality function thus represents the quality of the result r. The quality function selects the result r based in part on the privacy parameter $\varepsilon$, which enforces ($\varepsilon,\delta$)-differentially privacy on the selections.

Differential privacy may be provided by calculating the information gain of a split t, IG(t), in a differentially private manner. The information gain formula IG(t) can vary in different embodiments and may be based on the Information Gain Ratio, the Kullback-Leibler divergence, or on other factors.

In an embodiment, the information gain IG(t) of a split t is determined by:

$$IG(t) = -\sum_o \frac{n_o}{n_t} \log_2 \frac{n_o}{n_t} + \sum_i \frac{n_i}{n_t} \sum_o \frac{t_{io}}{n_i} \log_2 \frac{t_{io}}{n_i}$$

where $n_o$ is the number of tuples in the dataset having outcome o, $n_t$ is the number of tuples in the dataset having feature i, $t_{io}$ is the number of tuples in the dataset having both feature i and outcome o and $n_t$ is the total number of tuples in the dataset. That is, $$n_o = \sum_i t_{io}$$

$$n_i = \sum_o t_{io}$$

$$n_t = \sum_i n_i = \sum_o n_o$$

The sensitivity given by IG(t) is unbounded, and cannot be used directly in the exponential mechanism. However, because selecting a split aims to select the split with the highest information gain of the remaining (unselected) splits, IG(t) can be simplified to ignore constant terms, resulting in the quality function:

$$u(t) = -\sum_i n_i \sum_o \frac{t_{io}}{n_i} \log_2 \frac{t_{io}}{n_i}$$

where the sensitivity s(t) is given by:

$$s(t) = \log_2(n_i + 1) + \frac{1}{\log 2}$$

The exponential mechanism selects a split from the set of splits based on the score of each split, such as u(t) for the above embodiment, on a sensitivity of the quality function, such as s(t) for the above embodiment, and on one or more privacy parameters, such as $(\varepsilon, \delta)$, thereby providing differential privacy. For example, the exponential mechanism selects a split o with probability proportional to:

$$\exp\left(\frac{\varepsilon * \text{score}}{\text{sensitivity}}\right)$$

which for the above embodiment may be:

$$\exp\left(\frac{\varepsilon * u(t)}{s(t)}\right).$$

Differential privacy is added in this manner, using the exponential mechanism to select a split based on information gain, because rather than selecting the split with the highest information gain, that split merely has the highest probability of being selected. There is a chance another split, such as the split with the lower amount of information gain, will be selected.

Furthermore, upon a decision tree being trained, the specific count of each classification at each leaf node of the decision tree may be made differentially private. For example, after construction and training of the decision tree using training data, a differentially private count as described earlier may be performed at each leaf node for each classification category (otherwise known as "classification option"), thereby determining, for each leaf node, a differentially private number of tuples of the training data which were classified at that leaf node for each classification category. In an embodiment this is performed for each decision tree in a random forest classifier and the differentially private counts are returned in response to the query 108 in addition to the random forest classifier itself. This additional layer of differential privacy may be used to further safeguard restricted training data from adversaries, such as attempts to derive personally identifiable information of particular patients from a set of hospital data.

Depending upon the embodiment the random forest engine 316 may be used to generate one or more of a variety of different types of random forest classifiers. For example, the decision trees in the random forest classifier need not be binary decision trees. The decision trees can have any number of classification options and therefore in some embodiments more than two child nodes per parent node. In addition, the decision trees may have internal variation, such as a ternary layer followed by binary layers. The generated random forest classifiers may include multiple types of decision trees, such as both binary decision trees and ternary decision trees, or decision trees of varying height. Different decision trees within a random forest classifier may be constructed and/or trained on different subsets of the set of data.

Figure 15:
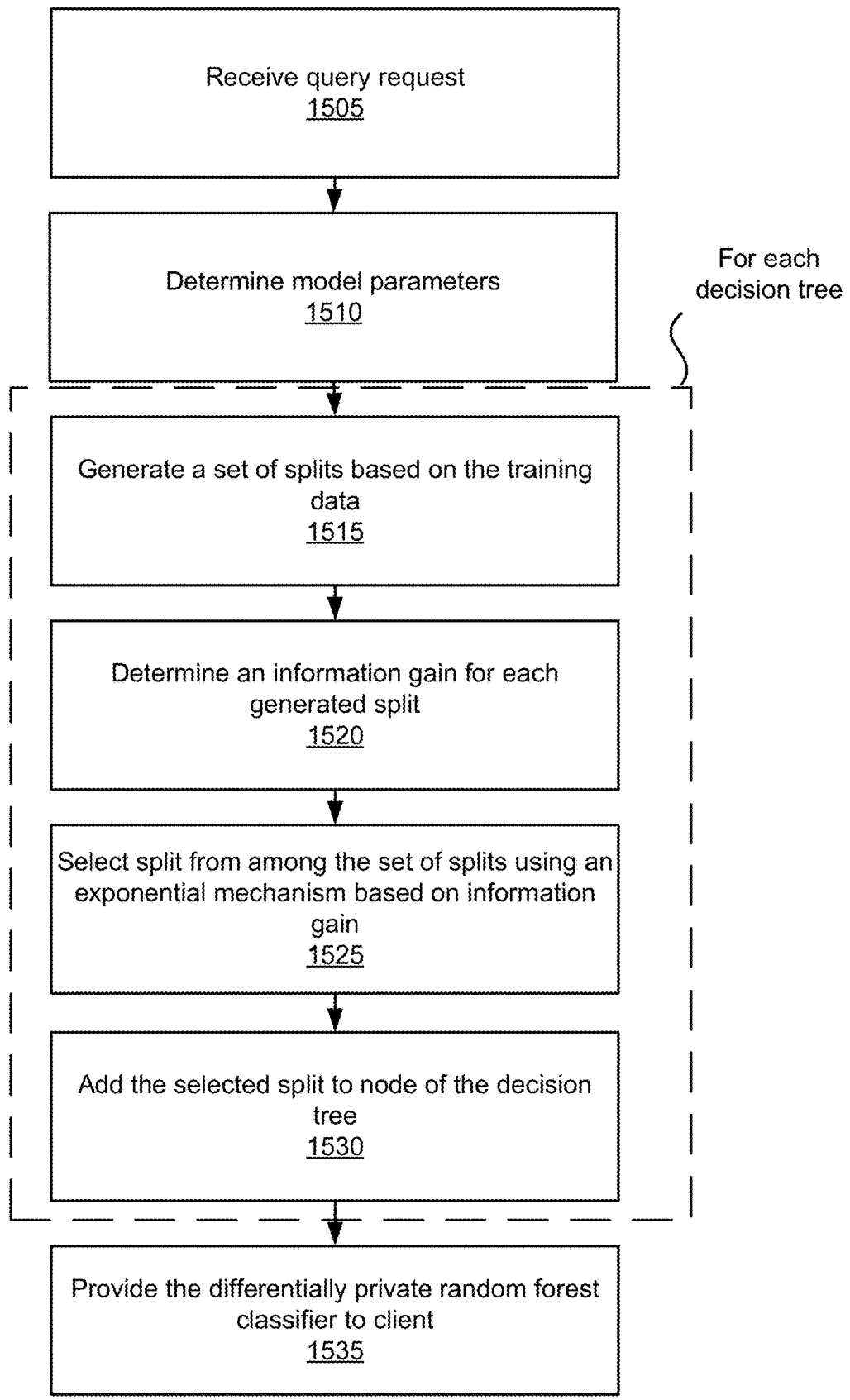
FIG. 15 illustrates a method for generating a differentially private random forest classifier, according to one embodiment.

FIG. 15 illustrates a method for generating a differentially private random forest classifier, according to one embodiment. FIG. 15 represents a special case of the method illustrated in FIG. 10 in which the database query requests a differentially private random forest classifier. As with FIG. 10, different embodiments can perform additional and/or different steps than those shown in FIG. 15. Additionally, other embodiments can perform the steps in different orders.

As shown in FIG. 15, the differentially private security system 102 receives 1505 a request from a client 104 to perform a query upon a set of restricted data. The query involves generating a random forest classifier in which the restricted data are used as training data. The request identifies a level of differential privacy.

The differentially private security system 102 determines 1510 model parameters associated with the query. The model parameters describe aspects of the random forest classifier to be generated in response to the query. The model parameters may indicate, for example, a number of decision trees to be used in the classifier, a number of splits to include in the decision trees, a maximum tree height, and a utility gain threshold. Model parameters may be based on the computational capabilities of the differentially private security system 102, such as the computation time and/or memory available to service the query. Model parameters may also be specified in terms of computational objectives, such as the desired accuracy of the classifier and/or the privacy parameters. In one embodiment the model parameters are specified by the query. In other embodiments, some or all of the model parameters are specified by the differentially private security system 102 (e.g., as default parameters).

As part of this determination 1510, the security system 102 identifies the number of decision trees to create for the random forest classifier. The number of decision trees may be explicitly specified as a model parameter or derived from other parameters. The security system 102 then uses the training data to generate the specified number of decision trees. Steps 1515-1530, described below, are iterated for each decision tree being generated.

To generate an individual tree, the differentially private security system 102 generates 1515 a set of splits based on the training data. The number of generated splits is determined from the model parameters. In one embodiment, the splits are determined based on randomly-selected features of tuples in the training data. For example, if a feature of tuples in the training data is "age" by year, a split may be "age >80" or "age <20." If a feature is continuous, the range of the feature may be binned, such as by random thresholds, a set of uniform thresholds, or by a set of recursive medians, and each bin may be considered a nominal feature for splitting. Nominal features may be determined based on uniform thresholds, such as at each whole number, forming bins such as a bin 1 for continuous features falling in the range 0-1, a bin 2 for continuous features falling in the range 1.01-2, a bin 3 for continuous features falling in the range 2.01-3, and so on; a split may be, for example, "bin number >2" or "continuous feature value $\geq 2$," mapping to continuous features with a value of at least 2.00.

The differentially private security system 102 determines 1520 an information gain for each generated split, using, for example, the techniques described above. The differentially private security system 102 then selects 1525 splits from among the set of splits using the exponential mechanism based at least in part on the information gain as described above. The selected splits are added 1530 to nodes in the decision tree. Splits are added in this manner until the decision tree reaches the size specified by the model parameters.

The multiple decision trees generated via iterations of the steps described above collectively form the trained differentially private random forest classifier. In one embodiment, the differentially private security system 102 provides 1535 the differentially private random forest classifier to the client 104 in response to the request. The security system 102 may also provide additional information associated with the trained classifier, such as a differentially private count for each classification at each leaf node of each decision tree in the set of decision trees, again as described above. An analyst using the client 104 may then use the classifier to classify new entities as having or not having specified conditions. For example, the analyst can use the classifier to determine whether a patient has a medical condition and/or whether a financial transaction is exceptional.

In some embodiments, rather than provide the trained classifier to the client 104, the classifier is maintained at the differentially private security system 102 or another system. The analyst may use the classifier by providing data describing new entities to the system maintaining the classifier and receiving classification results in response thereto.

Other Considerations

Some portions of the above description describe the embodiments in terms of algorithmic processes or operations. These algorithmic descriptions and representations are commonly used by those skilled in the data processing arts to convey the substance of their work effectively to others skilled in the art. These operations, while described functionally, computationally, or logically, are understood to be implemented by computer programs comprising instructions for execution by a processor or equivalent electrical circuits, microcode, or the like. Furthermore, it has also proven convenient at times, to refer to these arrangements of functional operations as modules, without loss of generality. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the disclosure. This description should be read to include one or at least one and the singular also includes the plural unless it is obvious that it is meant otherwise.

Upon reading this disclosure, those of skill in the art will appreciate still additional alternative structural and functional designs for a system and a process for receiving a query for a private database, and responding to the query by executing a differentially private version of the query on the private database. Thus, while particular embodiments and applications have been illustrated and described, it is to be understood that the described subject matter is not limited to the precise construction and components disclosed herein and that various modifications, changes and variations which will be apparent to those skilled in the art may be made in the arrangement, operation and details of the method and apparatus disclosed herein.

The invention claimed is:

1. A method, comprising:

receiving a request from a client to generate a differentially private random forest classifier trained using a set of restricted data stored by a private database system, the request identifying a level of differential privacy corresponding to the request, the identified level of differential privacy comprising privacy parameters $\varepsilon$ and $\delta$, wherein $\varepsilon$ describes a degree of information released about the set of restricted data due to the request and $\delta$ describes an improbability of the request satisfying ($\varepsilon$)-differential privacy;

generating the differentially private random forest classifier in response to the request, generating the classifier comprising:

determining a number of decision trees comprising the differentially private random forest classifier;

generating the determined number of decision trees, wherein a decision tree comprises a plurality of leaf nodes representing classification categories, and generating the decision tree comprises:
  generating a set of splits based on features of the set of restricted data;
  determining an information gain for each split of the set of splits;
  selecting a split from the set of splits using an exponential mechanism based at least in part on the determined information gains of the splits in the set and at least one of the privacy parameters;
  adding the selected split to the decision tree at a node; and
  determining, for a certain leaf node of the plurality of leaf nodes representing a certain classification category of the classification categories, a differentially private count of entities in the set of restricted data in the certain classification category; and
providing the differentially private random forest classifier to the client, the provided differentially private random forest classifier comprising the differentially private count of entities in the certain classification category represented by the certain leaf node.

2. The method of claim 1, wherein determining the information gain for a split of the set of splits comprises evaluating:

$$-\sum_i n_i \sum_o \frac{t_{io}}{n_i} \log_2 \frac{t_{io}}{n_i},$$

wherein $n_o$ is determined by:

$$\Sigma_i t_{io},$$

wherein $n_i$ is determined by:

$$\Sigma_o t_{io},$$

wherein $n_t$ is determined by either:

$$\Sigma_i n_i \text{ or } \Sigma_o n_o,$$

wherein o is a numeric representation of a classification category, i is a numeric representation of a feature of data in the set of restricted data, and $t_{io}$ is a number of data tuples in the set of restricted data having both the classification category represented by o and the feature represented by i.

3. The method of claim 2, wherein selecting a split from the set of splits using the exponential mechanism is further based on a sensitivity, wherein the sensitivity of the exponential mechanism is determined by:

$$\log_2(n_t + 1) + \frac{1}{\log 2}.$$

4. The method of claim 1, wherein generating the random forest classifier in response to the request is based on one or more model parameters, including at least one of a number of decision trees to be used in the classifier, a number of splits to include in the decision trees, a maximum tree height, and a utility gain threshold, and wherein each of the one or more model parameters is at least one of a default value and a value included in the request.

5. The method of claim 1,
  wherein the restricted data stores records comprising rows and columns;
  wherein the rows are associated with patients having a medical condition;
  wherein the columns contain values describing health data for the patients; and
  wherein providing the differentially private random forest classifier to the client comprises estimating whether a new patient has the medical condition.

6. The method of claim 1,
  wherein the set of data stores records comprising rows and columns;
  wherein the rows are associated with customers having a financial account;
  wherein the columns contain values describing financial data for the customers; and
  wherein providing the differentially private random forest classifier to the client comprises estimating whether a new customer can perform a financial transaction.

7. A non-transitory computer-readable storage medium storing computer program instructions executable by a processor to perform operations, the operations comprising:
  receiving a request from a client to generate a differentially private random forest classifier trained using a set of restricted data stored by a private database system, the request identifying a level of differential privacy corresponding to the request, the identified level of differential privacy comprising privacy parameters ε and δ, wherein ε describes a degree of information released about the set of restricted data due to the request and δ describes an improbability of the request satisfying (ε)-differential privacy;
  generating the differentially private random forest classifier in response to the request, generating the classifier comprising:
    determining a number of decision trees comprising the differentially private random forest classifier;
    generating the determined number of decision trees, wherein a decision tree comprises a plurality of leaf nodes representing classification categories, and generating the decision tree comprises:
      generating a set of splits based on features of the set of restricted data;
      determining an information gain for each split of the set of splits;
      selecting a split from the set of splits using an exponential mechanism based at least in part on the determined information gains of the splits in the set and at least one of the privacy parameters;
      adding the selected split to the decision tree at a node; and
      determining, for a certain leaf node of the plurality of leaf nodes representing a certain classification category of the classification categories, a differentially private count of entities in the set of restricted data in the certain classification category; and
  providing the differentially private random forest classifier to the client, the provided differentially private random forest classifier comprising the differentially private count of entities in the certain classification category represented by the certain leaf node.

8. The non-transitory computer-readable storage medium of claim 7, wherein determining the information gain for a split of the set of splits comprises evaluating:

$$-\sum_i n_i \sum_o \frac{t_{io}}{n_i} \log_2 \frac{t_{io}}{n_i},$$

wherein $n_o$ is determined by:

$$\Sigma_i t_{io},$$

wherein $n_i$ is determined by:

$$\Sigma_o t_{io},$$

wherein $n_t$ is determined by either:

$$\Sigma_i n_i \text{ or } \Sigma_o n_o,$$

wherein o is a numeric representation of a classification category, i is a numeric representation of a feature of data in the set of restricted data, and $t_{io}$ is a number of data tuples in the set of restricted data having both the classification category represented by o and the feature represented by i.

9. The non-transitory computer-readable storage medium of claim 8, wherein selecting a split from the set of splits using the exponential mechanism is further based on a sensitivity, wherein the sensitivity of the exponential mechanism is determined by:

$$\log_2(n_t + 1) + \frac{1}{\log 2}.$$

10. The non-transitory computer-readable storage medium of claim 7, wherein generating the random forest classifier in response to the request is based on one or more model parameters, including at least one of a number of decision trees to be used in the classifier, a number of splits to include in the decision trees, a maximum tree height, and a utility gain threshold, and wherein each of the one or more model parameters is at least one of a default value and a value included in the request.

11. The non-transitory computer-readable storage medium of claim 7,
wherein the restricted data stores records comprising rows and columns;
wherein the rows are associated with patients having a medical condition;
wherein the columns contain values describing health data for the patients; and
wherein providing the differentially private random forest classifier to the client comprises estimating whether a new patient has the medical condition.

12. The non-transitory computer-readable storage medium of claim 7,
wherein the set of data stores records comprising rows and columns;
wherein the rows are associated with customers having a financial account;
wherein the columns contain values describing financial data for the customers; and
wherein providing the differentially private random forest classifier to the client comprises estimating whether a new customer can perform a financial transaction.

13. A system comprising:
a processor for executing computer program instructions; and
a non-transitory computer-readable storage medium storing computer program instructions executable by the processor to perform operations comprising:
receiving a request from a client to generate a differentially private random forest classifier trained using a set of restricted data stored by a private database system, the request identifying a level of differential privacy corresponding to the request, the identified level of differential privacy comprising privacy parameters $\varepsilon$ and $\delta$, wherein $\varepsilon$ describes a degree of information released about the set of restricted data due to the request and $\delta$ describes an improbability of the request satisfying ($\varepsilon$)-differential privacy;
generating the differentially private random forest classifier in response to the request, generating the classifier comprising:
determining a number of decision trees comprising the differentially private random forest classifier;
generating the determined number of decision trees, wherein a decision tree comprises a plurality of leaf nodes representing classification categories, and generating the decision tree comprises:
generating a set of splits based on features of the set of restricted data;
determining an information gain for each split of the set of splits;
selecting a split from the set of splits using an exponential mechanism based at least in part on the determined information gains of the splits in the set and at least one of the privacy parameters;
adding the selected split to the decision tree at a node; and
determining, for a certain leaf node of the plurality of leaf nodes representing a certain classification category of the classification categories, a differentially private count of entities in the set of restricted data in the certain classification category; and
providing the differentially private random forest classifier to the client the provided differentially private random forest classifier comprising the differentially private count of entities in the certain classification category represented by the certain leaf node.

14. The system of claim 13, wherein determining the information gain for a split of the set of splits comprises evaluating:

$$-\sum_i n_i \sum_o \frac{t_{io}}{n_i} \log_2 \frac{t_{io}}{n_i},$$

wherein $n_o$ is determined by:

$$\Sigma_i t_{io},$$

wherein $n_i$ is determined by:

$$\Sigma_o t_{io},$$

wherein $n_t$ is determined by either:

$$\Sigma_i n_i \text{ or } \Sigma_o n_o,$$

wherein o is a numeric representation of a classification category, i is a numeric representation of a feature of data in the set of restricted data, and $t_{io}$ is a number of data tuples in the set of restricted data having both the classification category represented by o and the feature represented by i.

15. The system of claim 14, wherein selecting a split from the set of splits using the exponential mechanism is further based on a sensitivity, wherein the sensitivity of the exponential mechanism is determined by:

$$\log_2(n_t + 1) + \frac{1}{\log 2}.$$

16. The system of claim 13,
wherein the restricted data stores records comprising rows and columns;
wherein the rows are associated with patients having a medical condition;
wherein the columns contain values describing health data for the patients; and
wherein providing the differentially private random forest classifier to the client comprises estimating whether a new patient has the medical condition.

17. The system of claim 13,
wherein the set of data stores records comprising rows and columns;
wherein the rows are associated with customers having a financial account;
wherein the columns contain values describing financial data for the customers; and
wherein providing the differentially private random forest classifier to the client comprises estimating whether a new customer can perform a financial transaction.

* * * * *